US012127765B2

(12) United States Patent
Samuel et al.

(10) Patent No.: US 12,127,765 B2
(45) Date of Patent: Oct. 29, 2024

(54) BOTTOM LOADING POLYAXIAL SCREW

(71) Applicant: Life Spine, Inc., Huntley, IL (US)

(72) Inventors: Forrest Samuel, Carlsbad, CA (US); Gregory Palagi, Geneva, IL (US)

(73) Assignee: Life Spine, Inc., Huntley, IL (US)

( * ) Notice: Subject to any disclaimer, the term of this patent is extended or adjusted under 35 U.S.C. 154(b) by 960 days.

(21) Appl. No.: 17/150,865

(22) Filed: Jan. 15, 2021

(65) Prior Publication Data

US 2021/0128201 A1    May 6, 2021

Related U.S. Application Data

(63) Continuation-in-part of application No. 16/790,098, filed on Feb. 13, 2020, now Pat. No. 11,350,968, which is a continuation of application No. 15/947,848, filed on Apr. 8, 2018, now Pat. No. 10,588,666.

(60) Provisional application No. 62/483,590, filed on Apr. 10, 2017.

(51) Int. Cl.
*A61B 17/70* (2006.01)
*A61B 17/86* (2006.01)
*A61B 90/00* (2016.01)

(52) U.S. Cl.
CPC ...... *A61B 17/7032* (2013.01); *A61B 17/7037* (2013.01); *A61B 17/8605* (2013.01); *A61B 17/863* (2013.01); *A61B 2090/037* (2016.02)

(58) Field of Classification Search
CPC ............ A61B 17/7032; A61B 17/7034; A61B 17/7035; A61B 17/7037; A61B 17/8605
USPC .................................................. 606/264–270
See application file for complete search history.

(56) References Cited

U.S. PATENT DOCUMENTS

| 2,910,995 | A | 11/1959 | Candido |
| 8,628,558 | B2 | 1/2014 | Harvey et al. |
| 8,852,241 | B2 | 10/2014 | Datta |
| 9,707,013 | B2 * | 7/2017 | Rezach ............... A61B 17/7037 |
| 9,775,660 | B2 * | 10/2017 | Spratt ................. A61B 17/8685 |
| 9,883,892 | B2 * | 2/2018 | Jackson ............. A61B 17/7091 |
| 10,588,666 | B2 | 3/2020 | Samuel et al. |
| 2010/0160981 | A1 | 6/2010 | Butler et al. |

(Continued)

FOREIGN PATENT DOCUMENTS

EP    2 985 001 A1    2/2016

OTHER PUBLICATIONS

International Search Report for PCT/US2018/026646, Jun. 25, 2018, 5 pages.

*Primary Examiner* — Eduardo C Robert
*Assistant Examiner* — Christina Negrellirodriguez
(74) *Attorney, Agent, or Firm* — Foley & Lardner LLP

(57) ABSTRACT

A modular poly-axial bone screw includes a poly-axial bone screw, a poly-axial tulip head, and a collet disposed within the tulip head, the collet interacting with the bone screw and tulip head providing an interference fit with the bone screw head to lock orientation of the tulip head on and relative to the bone screw. Inner configurations of the tulip head interact with outer configurations of the collet to lock axial and/or rotational position of the collet within and relative to the tulip head, and thus about the bone screw head. The collet also has a base configured to conform to a top of a bone screw, wherein the collet is configured to support the bone screw and the tulip head when a spine rod is fixed in the tulip head.

20 Claims, 21 Drawing Sheets

(56) References Cited

U.S. PATENT DOCUMENTS

| | | |
|---|---|---|
| 2011/0106178 A1 | 5/2011 | Schwab |
| 2012/0143266 A1 | 6/2012 | Jackson et al. |
| 2014/0121703 A1 | 5/2014 | Jackson et al. |
| 2014/0135839 A1 | 5/2014 | Frankel et al. |
| 2014/0236239 A1* | 8/2014 | Biedermann ...... A61B 17/7037 606/278 |
| 2016/0331412 A1* | 11/2016 | Biedermann ...... A61B 17/7037 |
| 2018/0228516 A1 | 8/2018 | Armstrong et al. |

* cited by examiner

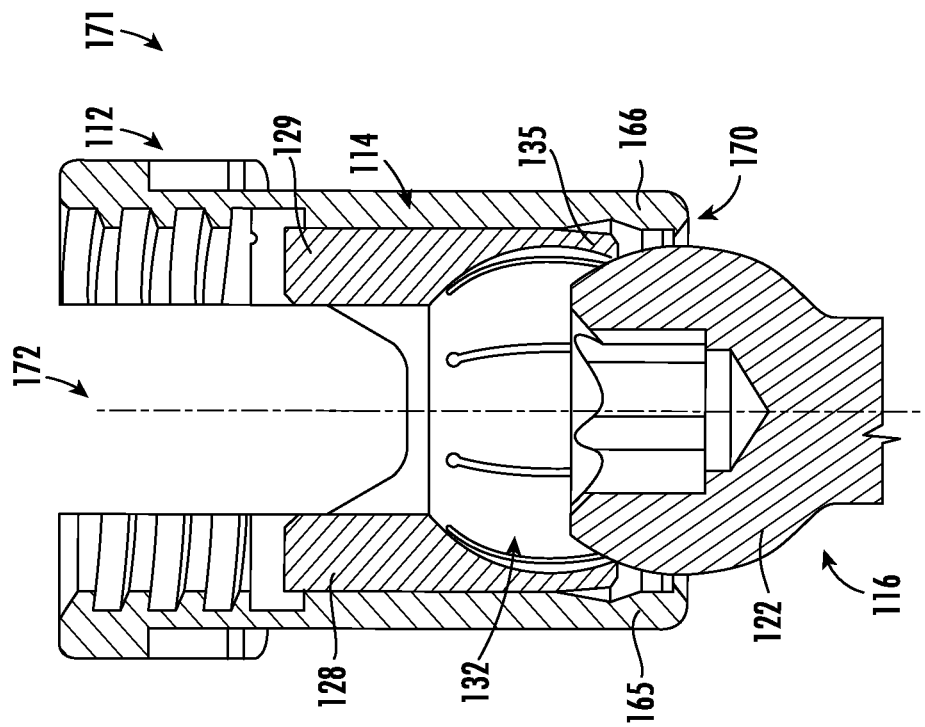
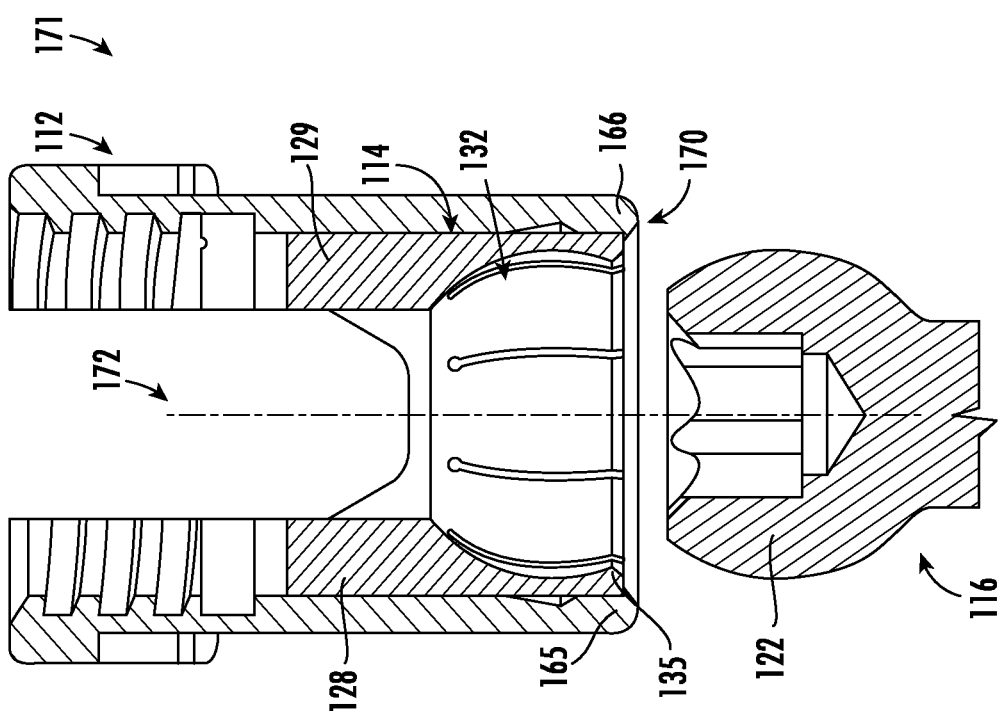

BOTTOM LOADING POLYAXIAL SCREW

CROSS-REFERENCE TO RELATED APPLICATIONS

This application is a continuation-in-part of U.S. application Ser. No. 16/790,098, filed Feb. 13, 2020, which is a continuation of U.S. application Ser. No. 15/947,848, filed Apr. 8, 2018, the entire contents of which is hereby incorporated herein by reference in its entirety, and which claims the benefit of and/or priority under 35 U.S.C. § 119(e) to U.S. Application No. 62/483,590, filed Apr. 10, 2017, the entire contents of which is hereby incorporated herein by reference.

BACKGROUND

The present invention relates to spine screw assemblies for spine fixation and, more particularly, to modular bone screw assemblies for spinal rod applications.

Many people contend with orthopedic issues as a result of age, disease, and trauma, as well as congenital and acquired complications and conditions. While some of these issues can be alleviated without surgery, other issues respond better to surgery. In some cases, surgery may include the insertion of an orthopedic implant. Orthopedic spine assemblies and constructs such as spine plates, bone screw assemblies for spinal rods and other devices (spinal components) have made a profound contribution to the correction of spinal deformities, accidents and other problems in the cervical as well as thoracic, lumbar and sacral spine. These and other spinal devices are typically fixed to vertebrae using vertebral bone screws. Vertebral bone screws are specially designed and manufactured bone screws that are placed into the bone of a vertebra. Vertebral bone screws placed in the vertebra offer superior strength and pull-out resistance as compared to other forms of fixation in spine surgery. The ability to achieve vertebral fixation has allowed surgeons to obtain more secure fixation of the spinal components involved, which permits more powerful correction of spine problems and reported better clinical outcomes.

In addition to other uses, bone screws provide a solid foundation for the attachment of spinal rods. Spine rods are used for the fixation of a plurality of vertebrae for various situations. A spine rod is held relative to the vertebrae by a spine rod bone screw assembly. Various types of spine rod bone screw assemblies are known such as those that allow for inter-operative adjustments in the coronal, transverse and sagittal planes—generally known as poly-axial spine rod bone screw assemblies. Certain spine rod bone screw assemblies allow for various degrees of freedom of attachment of a spine rod thereto from any direction, angle, and height. In all cases, however, the spine rod bone screw assemblies hold a spine rod and are fixed to a vertebra. The poly-axial spine rod bone screw assembly thus permits spine rods to be rigidly locked into a variety of positions along with other types of implant components. This allows a surgeon to tailor-make each construct.

One type of poly-axial spine rod bone screw assembly is known as a poly-axial tulip head spine rod holder. The poly-axial tulip head spine rod holder includes a poly-axial bone screw, a poly-axial head that is shaped like a tulip (poly-axial tulip head), and an insert within the poly-axial tulip head. The poly-axial tulip head is situated about the poly-axial bone screw head while the insert is situated within the poly-axial tulip head, the insert that interacts with the bone screw head and the tulip head. Downward pressure exerted against the insert during installation of a spine rod and set screw in the poly-axial tulip head causes the insert to bind against the poly-axial bone screw head and between the poly-axial tulip head such that the orientation of the tulip head is fixed relative to the bone screw. While current poly-axial tulip head spine rod holders are adequate, there is room for improvement.

Thus, there is a need for an improved poly-axial tulip head spine rod bone screw assembly.

SUMMARY

A modular poly-axial bone screw/screw assembly has three components, a poly-axial bone screw, a poly-axial tulip head, and an insert forming a collet disposed within the tulip head, the collet interacting with the tulip head to lock axial orientation of the collet within the tulip head and to provide a frictional interference fit with the bone screw head in order to lock orientation of the tulip head on and relative to the bone screw.

The tulip head has an inner configuration that interacts with the outer configuration of the collet to lock axial and/or rotational position of the collet within and relative to the tulip head, and thus about the bone screw head. The collet also has a resilient, tapered base with a plurality of slots in and about its end that allow the end to elastically splay outwardly over and upon the head of the bone screw to create a snap or frictional interference fit between the splayed collet and the bone screw head when a spine rod is fixed in the tulip head. An increase in spherical coverage created by the present configuration increases the amount of surface contact of the collet with the bone screw head. This allows for more controlled, uniform and secure orientation of the tulip head with respect to the bone screw.

In one form, the inner configuration of the tulip head comprises a plurality of projections protruding radially inwardly and spaced about the inner circumferential wall of the tulip head, while the outer configuration of the collet comprises a like plurality of depressions formed into its outer circumferential wall to receive the plurality of projections. Elastic deformation snap fits the collet within the tulip head. In another form, the plurality of projections are situated on the collet, and the plurality of depressions are situated in the inner circumferential wall of the tulip head, while the plurality of projections are situated on the outer conferential wall of the collet.

In another form, the inner configuration of the tulip head comprises a radially inwardly projecting lip extending about the inner circumferential wall of the tulip head creating an overhang and an undercut, while the outer configuration of the collet comprises a circumferential ledge. Other means may be used to lock the axial and/or rotational position of the collet in and to the tulip head.

The collet has an elastic/resilient base created at least in part by a plurality of cuts, slots, cutouts or the like that allows the poly-axial bone screw head to snap into the base of the collet thus causing a frictional interference fit. Particularly, the plurality of cuts in the base allows the elastic/resilient base of the collet to splay slightly during reception of the poly-axial bone screw head, then conform about the poly-axial bone screw head once pressure is applied by insertion of a spine rod and set screw into the tulip head, while the tapered end binds around, between and against the bone screw head and the inner wall of the tulip head.

In another form, the modular poly-axial bone screw assembly may include a c-clip configured for coupling to a bottom portion of the bone screw head and retained within the bottom of the tulip head. In this form, the collet of the modular poly-axial bone screw assembly includes a contoured base, which is configured to conform to the top portion of the bone screw head. The collet may further include one or more channels disposed within an outer surface of the collet and configured to engage with one or more corresponding protruding portions of the tulip head to retain the collet therein. Once assembled, the modular poly-axial bone screw assembly is configured such that the c-clip is coupled to the bottom portion of the bon screw head via an interference fit and retained within a recess of the tulip head, and the collet is positioned upon a top portion of the bone screw head and disposed within a central bore of the tulip head, engaging with protruding members thereof.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The above mentioned and other features, advantages and objects of this invention, and the manner of attaining them, will become apparent and the invention itself will be better understood by reference to the following description of forms of the invention taken in conjunction with the accompanying drawings, wherein:

FIG. 29 is a cross-sectional view of the modular poly-axial bone screw assembly of FIG. 11 taken along line 28-28 of FIG. 27, wherein the collet and tulip head assembly is in a separated configuration;

FIG. 30 is a cross-sectional view of the modular poly-axial bone screw assembly of FIG. 29, taken along 28-28 of FIG. 27, wherein the collet and tulip head assembly is in an intermediate configuration;

A description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Figure 10:
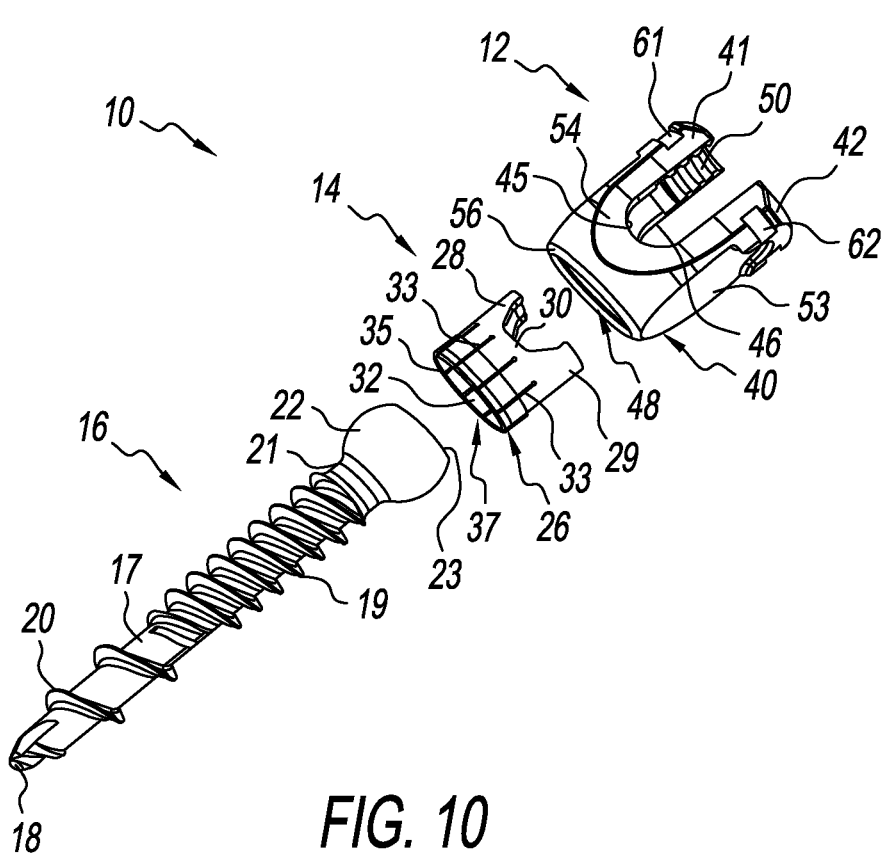
FIG. 10 is an exploded view of the modular poly-axial bone screw assembly of FIG. 1.
Figure 11:
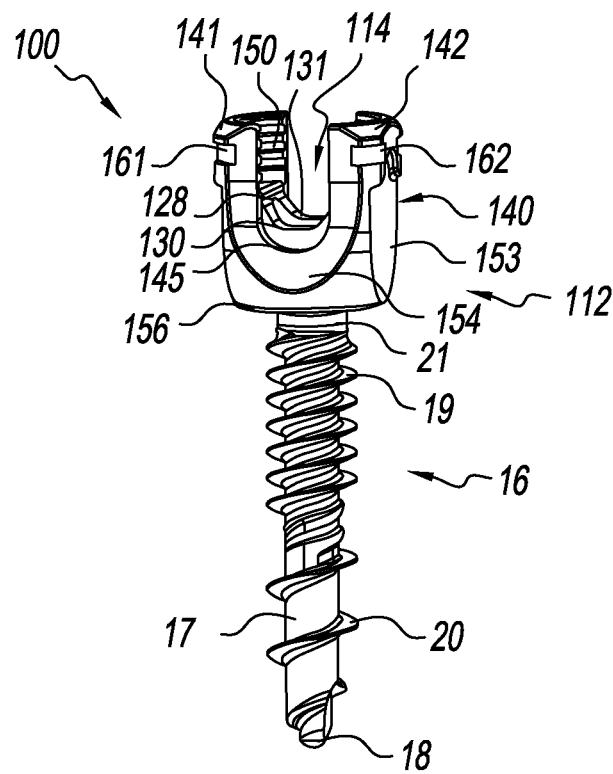
FIG. 11 is an isometric view of another form of a modular poly-axial bone screw assembly fashioned in accordance with the present principles.
Figure 12:
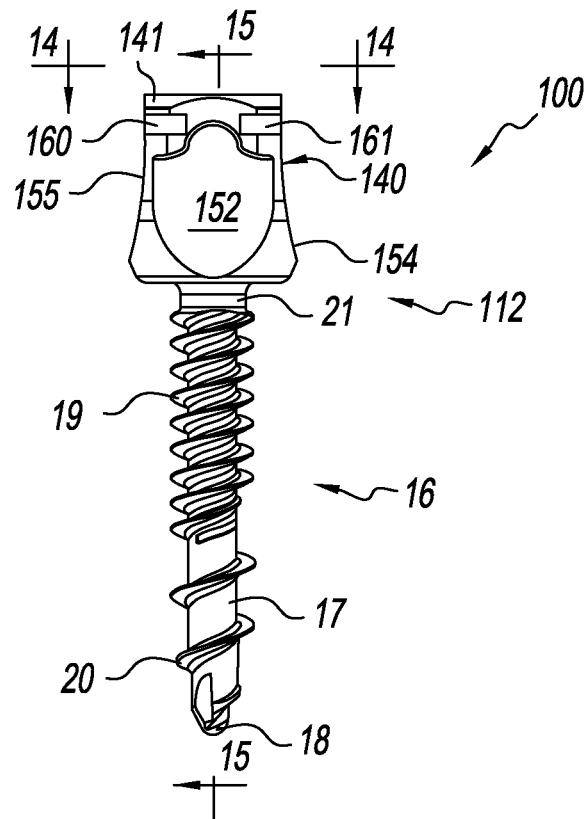
FIG. 12 is a side view of the modular poly-axial bone screw assembly of FIG. 11.
Figure 13:
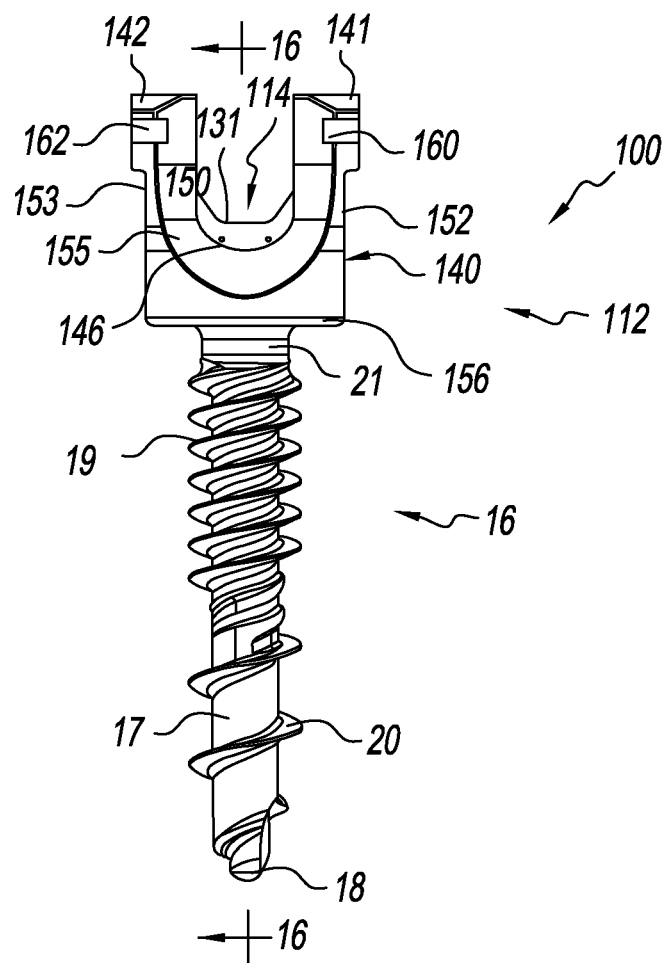
FIG. 13 is a another side view of the modular poly-axial bone screw assembly of FIG. 11, 90° to the side view of FIG. 11.
Figure 14:
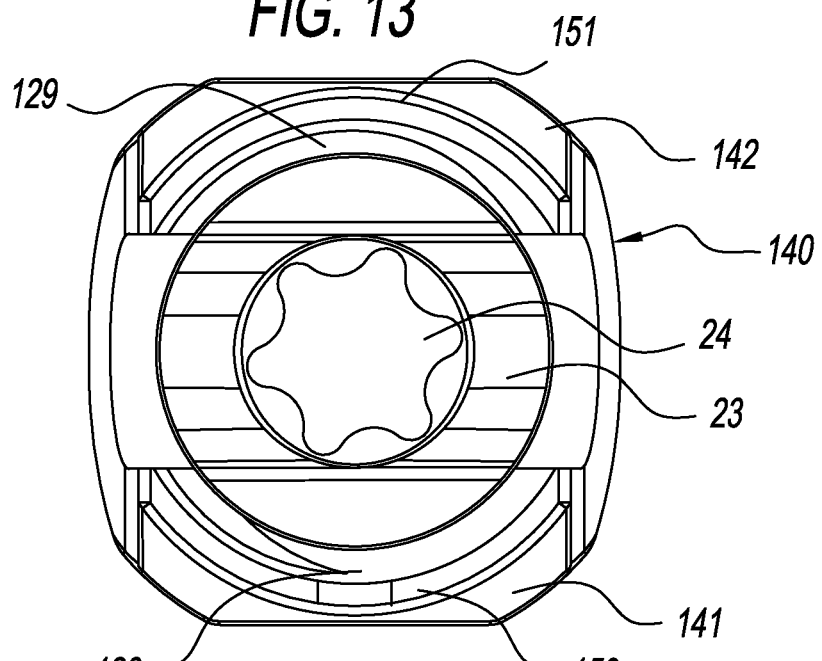
FIG. 14 is an enlarged top view of the modular poly-axial bone screw assembly of FIG. 11 taken along line 14-14 of FIG. 12.
Figure 15:
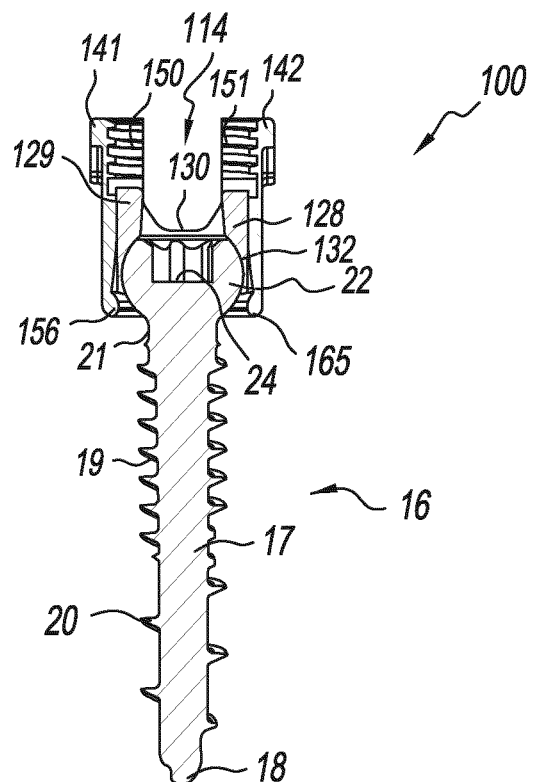
FIG. 15 is a sectional view of the modular poly-axial bone screw assembly of FIG. 11 taken along line 15-15 of FIG. 12.
Figure 16:
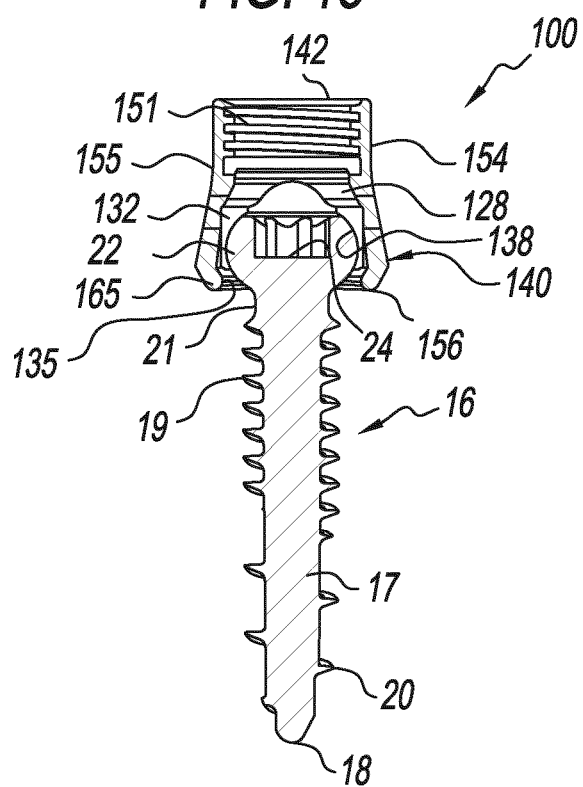
FIG. 16 is a sectional view of the modular poly-axial bone screw assembly of FIG. 11 taken along line 16-16 of FIG. 13.

Referring to FIGS. 1-10, there is depicted a form of modular poly-axial (polyaxial) bone screw/screw assembly ("modular poly-axial bone screw"), generally designated 10, for use in the spine and fashioned as described in the above Summary of the Invention, the modular poly-axial bone screw assembly 10 for holding a spine rod (not shown) relative to the spine (not shown). FIG. 10 shows the three components of the poly-axial bone screw assembly 10 in an exploded or pre-assembled view, the assemblage comprising a poly-axial bone screw ("bone screw") 16, a tulip head 12, and an insert/collet ("collet") 14.

The bone screw 16 has a generally globular (and therefore poly-axial) head 22 with a socket 24 in a top of the head 22 that is configured to receive a bone screw installation tool (not shown). In one form, the socket 24 is hexalobe-shaped and configured to receive a hexalobe bone screw installation tool. Other socket configurations may be used. A circumferential angle, slant, or taper 25 is preferably, but not necessarily, provided about the socket 24. A neck 21 projects from the head 22 opposite the socket 24. A shank 17 extends axially from the neck 21 and terminates in a tip 23. The shank 17 has first external threads/threading 20 along a lower portion of its axial length ("lower threading") proximate the tip 18, and second external threads/threading 19 along an upper portion of its axial length between the lower threading 20 and the neck 21. The shaft preferably, but not necessarily, increases in diameter from the tip 18 to the neck 21.

The tulip head 12 is defined by a generally tulip shaped body 40, having a bottom 56, a first side or sidewall 41 and a second side or sidewall 42, the second sidewall 42 opposite the first sidewall 41, the nomenclature first and second being arbitrary here and throughout unless otherwise indicated. The first sidewall 41 is generally arc-shaped and includes threads/threading 50 on its interior wall/surface. The second sidewall 42 is generally arc-shaped and includes threads/threading 51 on its interior wall/surface. The internal threading 50, 51 accepts a set screw (not shown) for fully seating the spine rod in the tulip head. The first sidewall 41 has an arcuate top 43 that is preferably, but not necessarily, sloped or slanted radially inwardly, and the second sidewall 41 likewise has an arcuate top 44 that is preferably, but not necessarily, sloped or slanted radially inwardly. The first sidewall 41 has a first flat 52 on its exterior surface extending generally from proximate the top 43 to the bottom 56. The first sidewall 41 further has a first notch 60 on one lateral side of the sidewall 41 proximate the top 43, and a second notch 61 on the other lateral side of the sidewall 41 proximate the top 43, the first and second notches permitting receipt of an installation tool (not seen) and otherwise. In like manner, the second sidewall 42 has a second flat 53 on its exterior surface extending generally from proximate the top 44 to the bottom 56. The second sidewall 42 further has a third notch 62 on one lateral side of the sidewall 42 proximate the top 44, and a fourth notch 63 on the other lateral side of the sidewall 42 proximate the top 44. The lower portion 64 of the body 40 is generally rounded.

The tulip head 12 has an interior bore 48 extending from a top to and through a bottom 56 of the body 40. The bore 48 receives the bone screw 16 and the collet 14. A spine rod reception area is defined in the body 40, formed as a first pocket, cutout or notch 45 between lateral sides of the first sidewall 41 and the second sidewall 42, and a second pocket, cutout or notch 46 between lateral sides of the first sidewall 41 and the second sidewall 42, the first and second pockets are opposite one another. The first and second notches 45, 46 are formed to receive a spine rod therein (not shown) and thus are generally arcuate or cup-shaped. The outside of the body 40 of the tulip head 12 surrounding the first notch 45 is a flat 54, while the outside of the body 40 of the second notch 46 is a flat 53. The internal threading 50, 51 of the first and second sidewalls 41, 42, provide for reception of a set screw or the like (not shown) that is used to "lock up" the tulip head 12 on and relative to the bone screw 16 via the collet 14.

Figure 1:
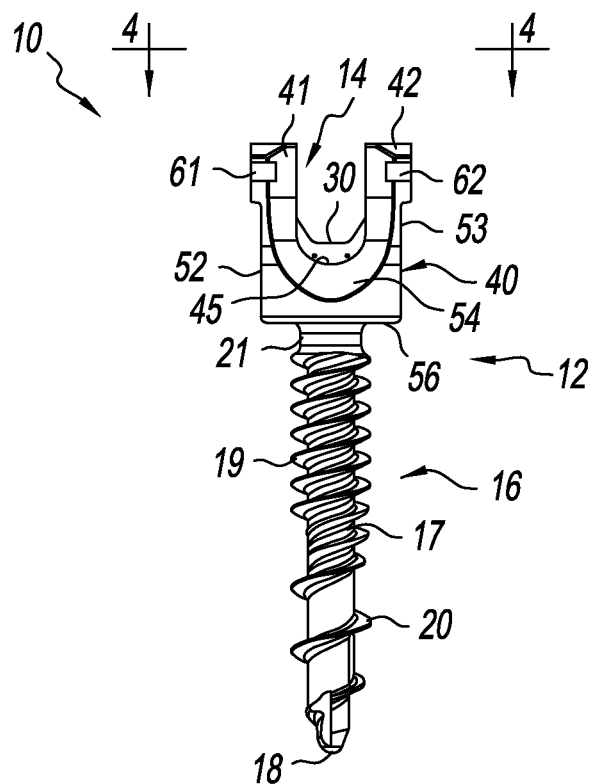
FIG. 1 is a side view of a form of a modular poly-axial bone screw assembly fashioned in accordance with the principles of the present invention.
Figure 2:
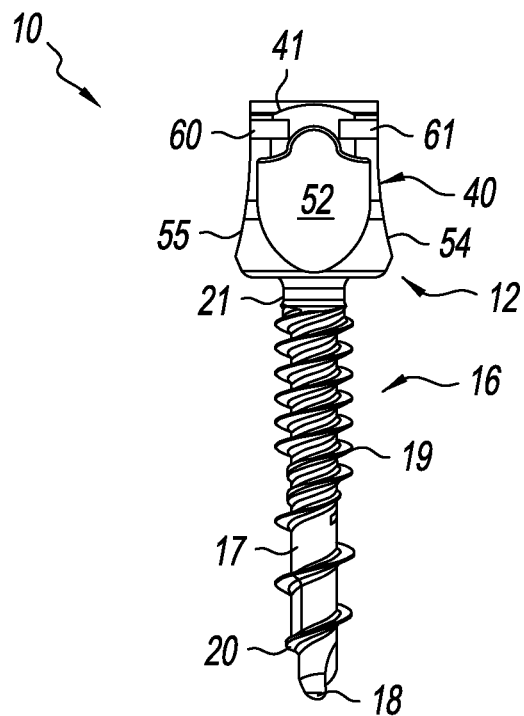
FIG. 2 is another side view of the modular poly-axial bone screw assembly of FIG. 1, 90° to the side view of FIG. 1.
Figure 3:
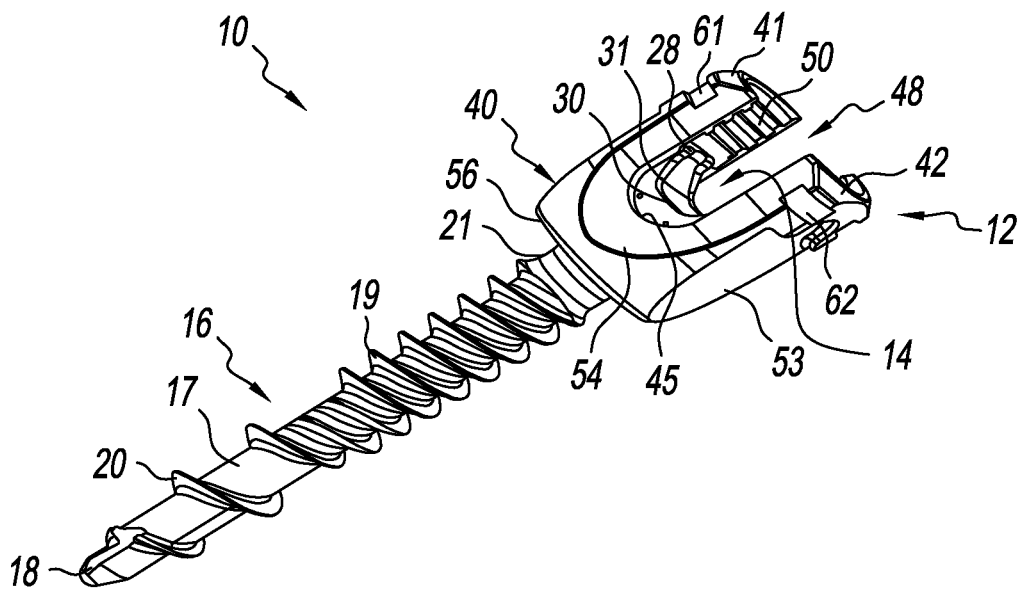
FIG. 3 is an isometric angled view of the modular poly-axial bone screw assembly of FIG. 1.
Figure 4:
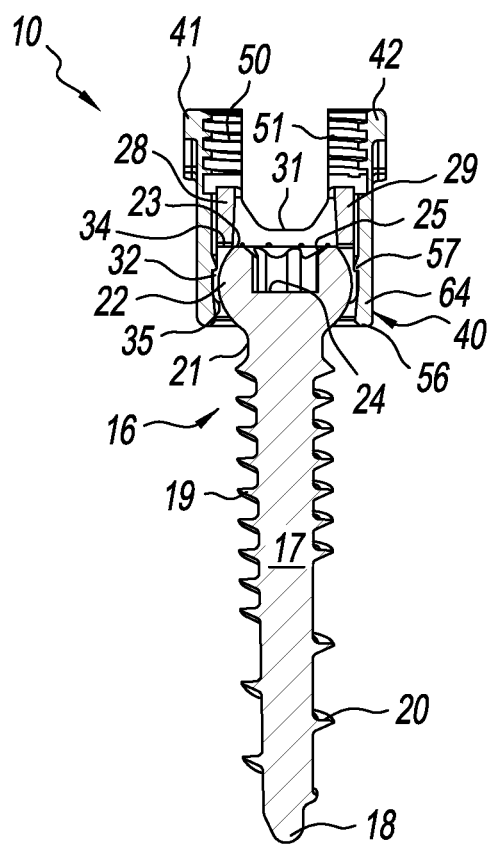
FIG. 4 is a sectional view of the modular poly-axial bone screw assembly of FIG. 1 taken along line 4-4 of FIG. 4.
Figure 5:
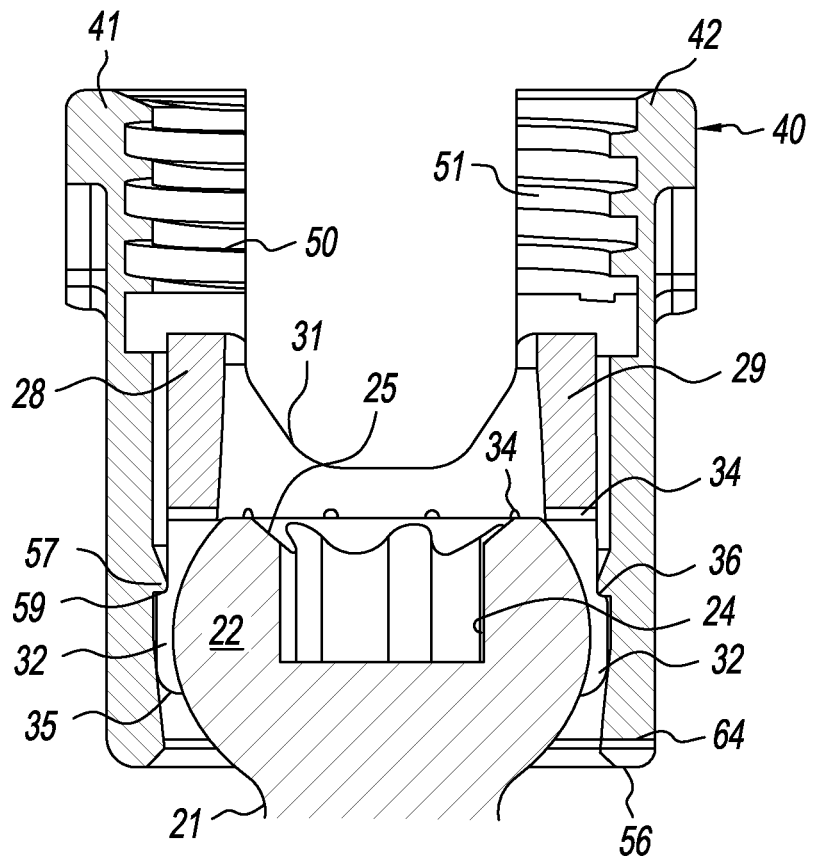
FIG. 5 is an enlarged sectional view of the tulip head and collet situated on the bone screw head of the modular poly-axial bone screw assembly of FIG. 1.
Figure 6:
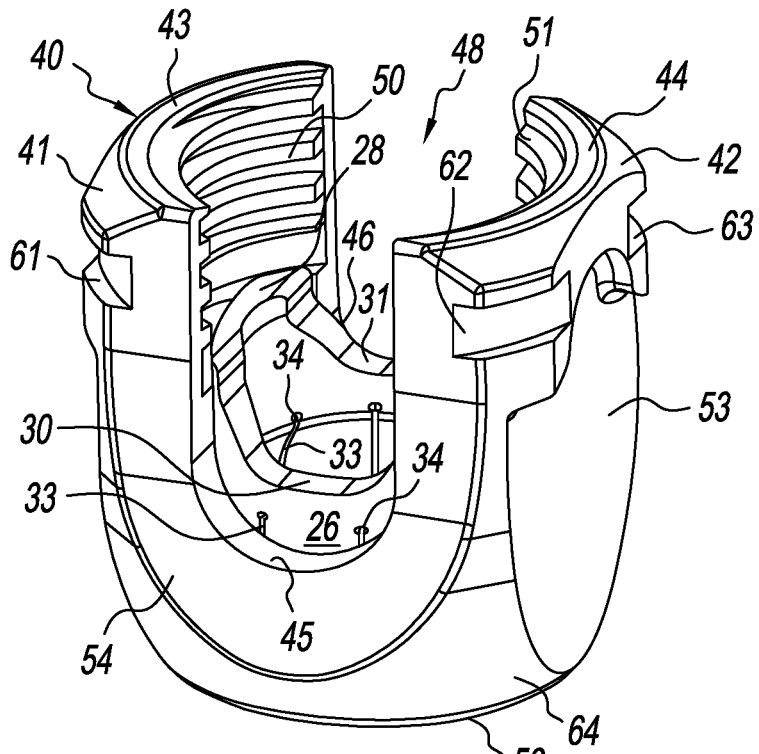
FIG. 6 is an enlarged isometric view of the collet assembled in the tulip head of the modular poly-axial bone screw assembly of FIG. 1.
Figure 7:
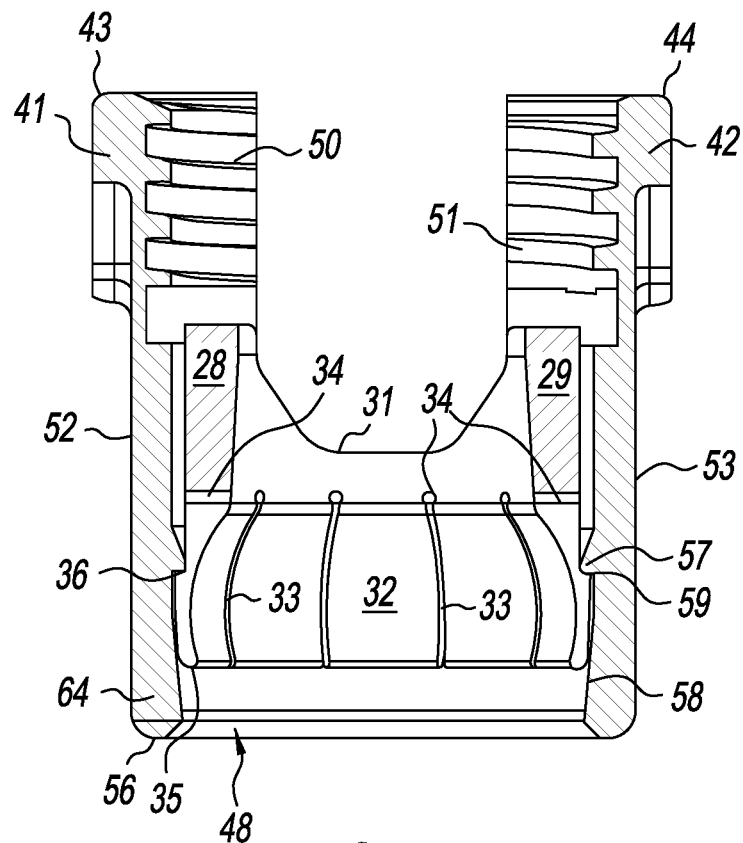
FIG. 7 is an enlarged sectional view of the assembled collet and tulip head of the modular poly-axial bone screw assembly of FIG. 1.
Figure 8:
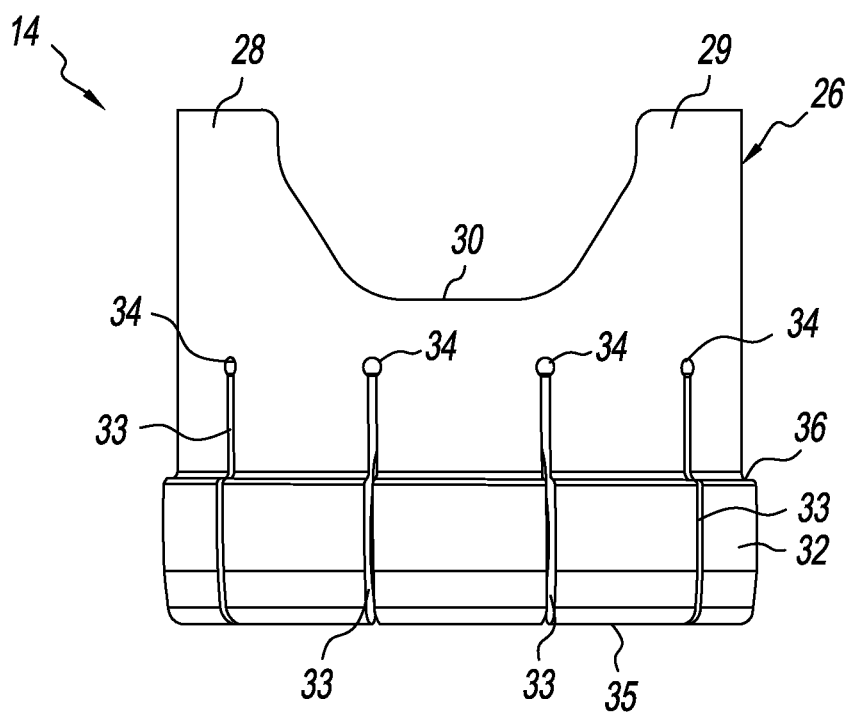
FIG. 8 is an enlarged side view of the collet of the modular poly-axial bone screw assembly of FIG. 1.
Figure 9:
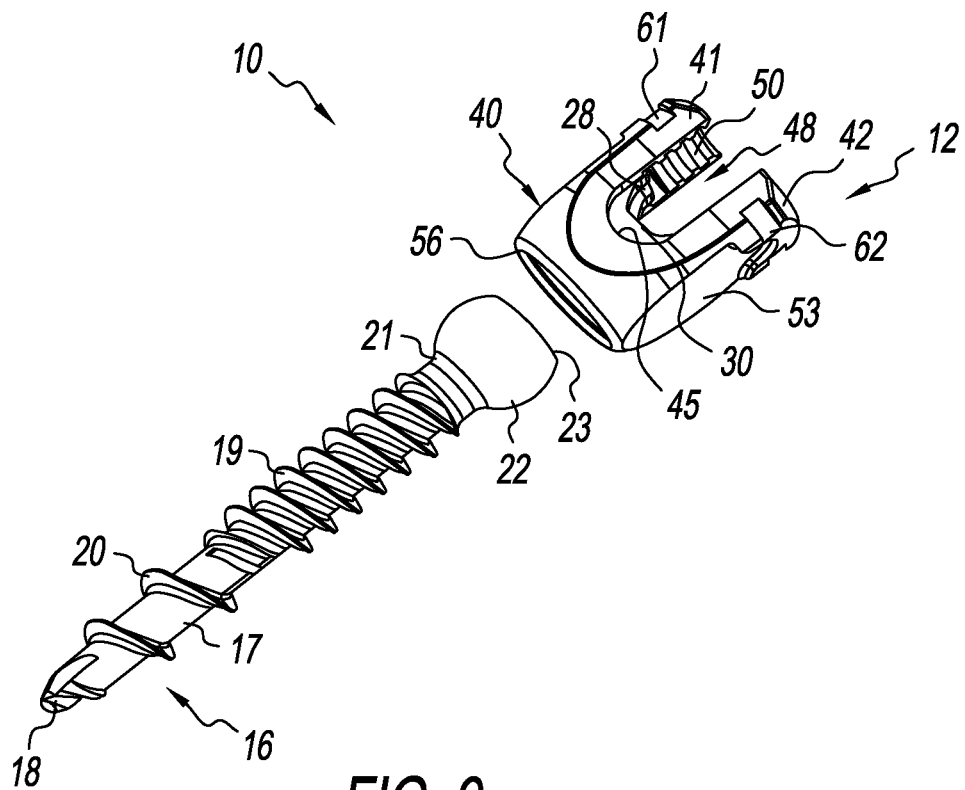
FIG. 9 is an exploded view of the assembled collect and tulip head relative to the bone screw of the modular poly-axial bone screw assembly of FIG. 1.

The inside of the tulip head 12 has an inner configuration best discerned in FIG. 5. Particularly, the inner configuration comprises a circumferential, radially inwardly projecting lip 57 extending about the lower inner circumferential wall of the tulip head, thereby creating an overhang and an undercut 59. Moreover, as discerned in the figure, the annular lower sidewall of the body 40 is preferably, but not necessarily, wider at the bottom 56.

The insert/collet 14 provides a taper lock and is defined by a generally cylindrical body 26 having a bottom area 32 with a base or skirt on a lower portion thereof, a first upstanding flange, side or sidewall 28, and a second upstanding flange, side or sidewall 29 that define a first pocket, cutout or notch 30 between lateral sides of the first and second upstanding flanges 28, 29, and a second pocket, cutout or notch 31 between opposite lateral sides of the first and second upstanding flanges 28, 29, the notches 30, 31 thus being oppositely disposed. The first and second notches 30, 31 are formed to receive a spine rod therein (not shown) and thus are generally arcuate or cup-shaped. An interior bore extends from a top of the body to a bottom 35 of the body. The bore allows access to the socket 24 of the bone screw head 22 of the poly-axial bone screw 16.

The bottom area 32 of the collet 14 includes a plurality of cuts, cutouts, notches or the like 33 that extend axially from the bottom 35 towards the upstanding flanges 28, 29. Each cut 33 is preferably, but not necessarily, equally circumferentially spaced about the bottom area 32 of the body 26 and terminates axially in a hole 34. The cuts 33 create a collet mechanism that allows the screw head 22 to snap into the bottom area 32 of the collet 14 thus creating a frictional interference fit. It should be appreciated that the number of cuts 33 may vary from two (2) to as many as desired. It is also preferable, but not necessary, that the cuts 33 are evenly spaced about the bottom area 32. The cuts 33 create a resilient or elastic interference or snap on fit with the polyaxial screw head 22 by allowing the bottom area 32 to splay slightly then from back around the screw head 22. The spherical coverage of the head 22 increases the amount of surface contact between the bottom area 32 of the collet 14 and the polyaxial screw head 22.

The outside of the collet 14 has an outer configuration best discerned in FIG. 5. Particularly, the outer configuration comprises a ledge 36 extending circumferentially about the body 26 proximate the bottom area 32. Because of the elastic nature of the collet 14, the projecting lip 57 of the tulip head 12 is captured by/on the ledge 36.

Referring to FIGS. 11-28, there is depicted another form of a modular poly-axial (polyaxial) bone screw/screw assembly ("modular poly-axial bone screw"), generally designated 100, for use in the spine and fashioned as described in the above Summary of the Invention, the modular poly-axial bone screw assembly 100 for holding a spine rod (not shown) relative to the spine (not shown). In like form as the modular poly-axial bone screw assembly 10 of FIGS. 1-10, the modular poly-axial bone screw assembly 100 has three components, namely the poly-axial bone screw ("bone screw") 16 as described above, a tulip head 112, and an insert/collet ("collet") 114.

The tulip head 112 is defined by a generally tulip shaped body 140, having a bottom 156, a first side or sidewall 141 and a second side or sidewall 142, the second sidewall 142 opposite the first sidewall 141, the nomenclature first and second being arbitrary here and throughout unless otherwise indicated. The first sidewall 141 is generally arc-shaped and includes threads/threading 150 on its interior wall/surface. The second sidewall 142 is generally arc-shaped and includes threads/threading 151 on its interior wall/surface. The internal threading 150, 151 accepts a set screw (not shown) for fully seating the spine rod in the tulip head. The first sidewall 141 has an arcuate top 143 that is preferably, but not necessarily, sloped or slanted radially inwardly, and the second sidewall 141 likewise has an arcuate top 144 that is preferably, but not necessarily, sloped or slanted radially inwardly. The first sidewall 141 has a first flat 152 on its exterior surface extending generally from proximate the top 143 to the bottom 156. The first sidewall 141 further has a first notch 160 on one lateral side of the sidewall 141 proximate the top 143, and a second notch 161 on the other lateral side of the sidewall 141 proximate the top 143, the first and second notches permitting receipt of an installation tool (not seen) and otherwise. In like manner, the second sidewall 142 has a second flat 153 on its exterior surface extending generally from proximate the top 144 to the bottom 156. The second sidewall 142 further has a third notch 162 on one lateral side of the sidewall 142 proximate the top 144, and a fourth notch 163 on the other lateral side of the sidewall 142 proximate the top 144. The lower portion 164 of the body 140 is generally rounded.

The tulip head 112 has an interior bore 148 extending from a top to and through a bottom 156 of the body 120. The bore 148 receives the bone screw 116 and the collet 114. A spine rod reception area is defined in the body, formed as a first pocket, cutout or notch 145 between lateral sides of the first sidewall 141 and the second sidewall 142, and a second pocket, cutout or notch 146 between lateral sides of the first sidewall 141 and the second sidewall 142, the first and second pockets are opposite one another. The first and second notches 145, 146 are formed to receive a spine rod therein (not shown) and thus are generally arcuate or cup-shaped. The outside of the body 140 of the tulip head 112 surrounding the first notch 145 is a flat 154, while the outside of the body 140 of the second notch 146 is a flat 153. The internal threading 150, 151 of the first and second sidewalls 141, 142, provide for reception of a set screw or the like (not shown) that is used to "lock up" the tulip head 112 on and relative to the bone screw 116 via the collet 114.

Figure 17:
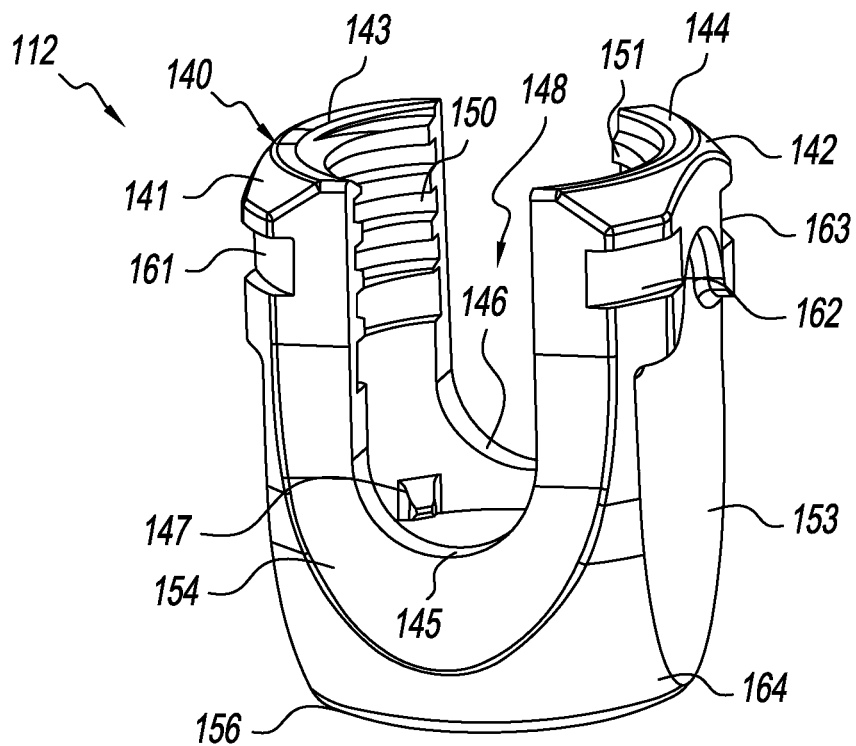
FIG. 17 is an enlarged isometric view of the tulip head of the modular poly-axial bone screw assembly of FIG. 11.
Figure 18:
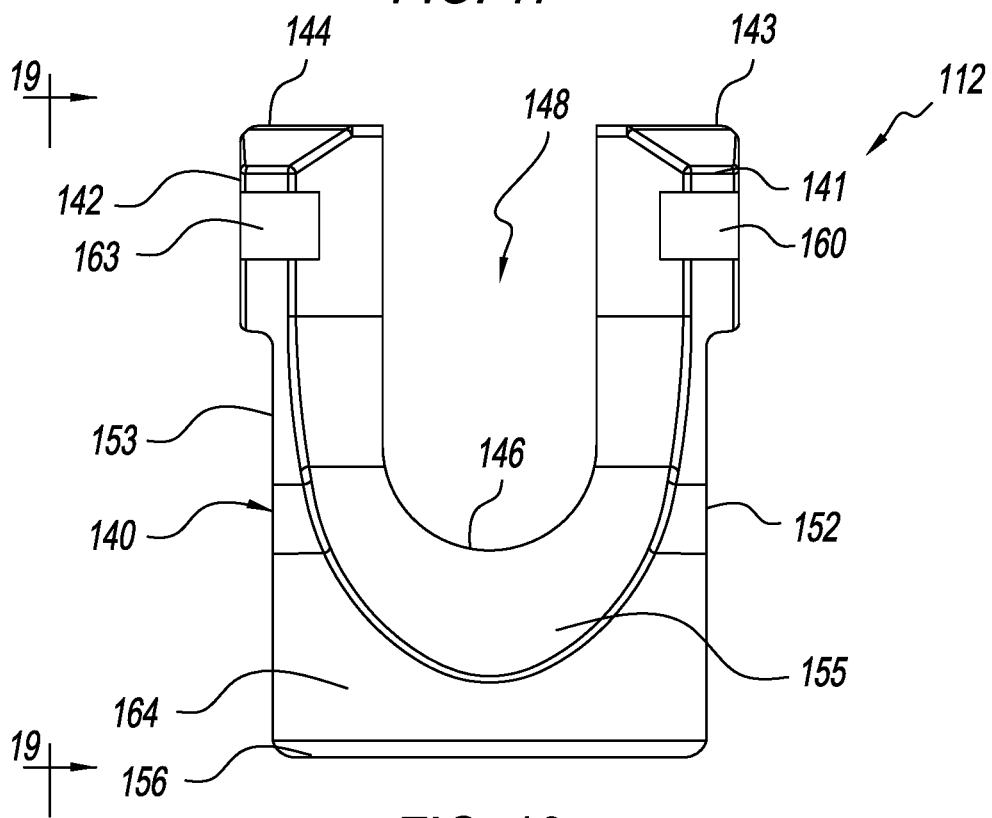
FIG. 18 is an enlarged side view of the tulip head of the modular poly-axial bone screw assembly of FIG. 11.
Figure 19:
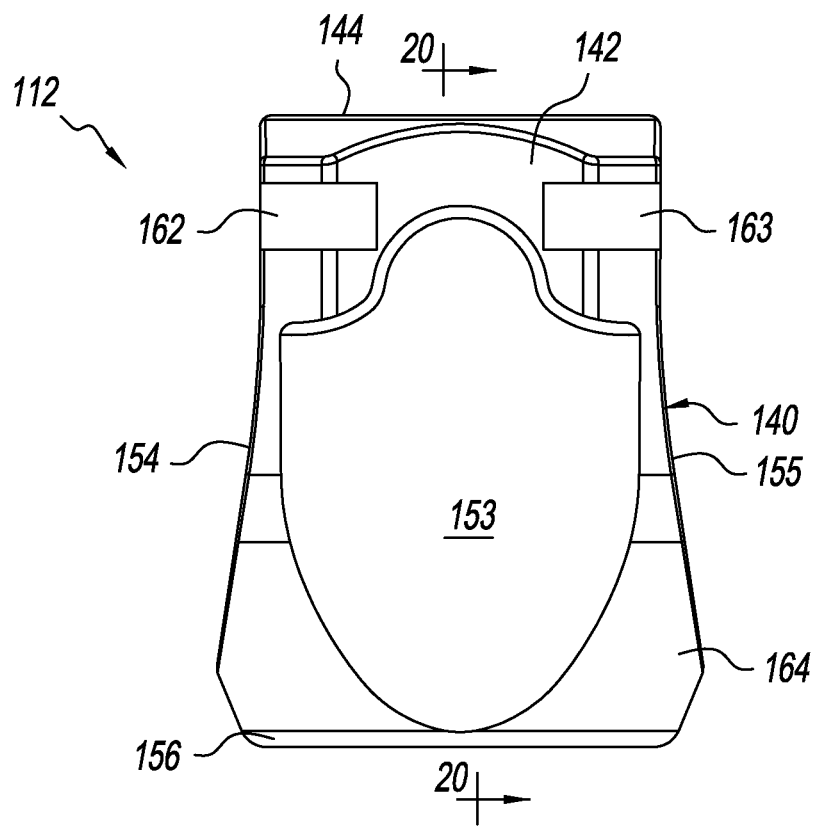
FIG. 19 is another side view of the tulip head of the modular poly-axial bone screw assembly of FIG. 11 taken along line 19-19 of FIG. 18.
Figure 20:
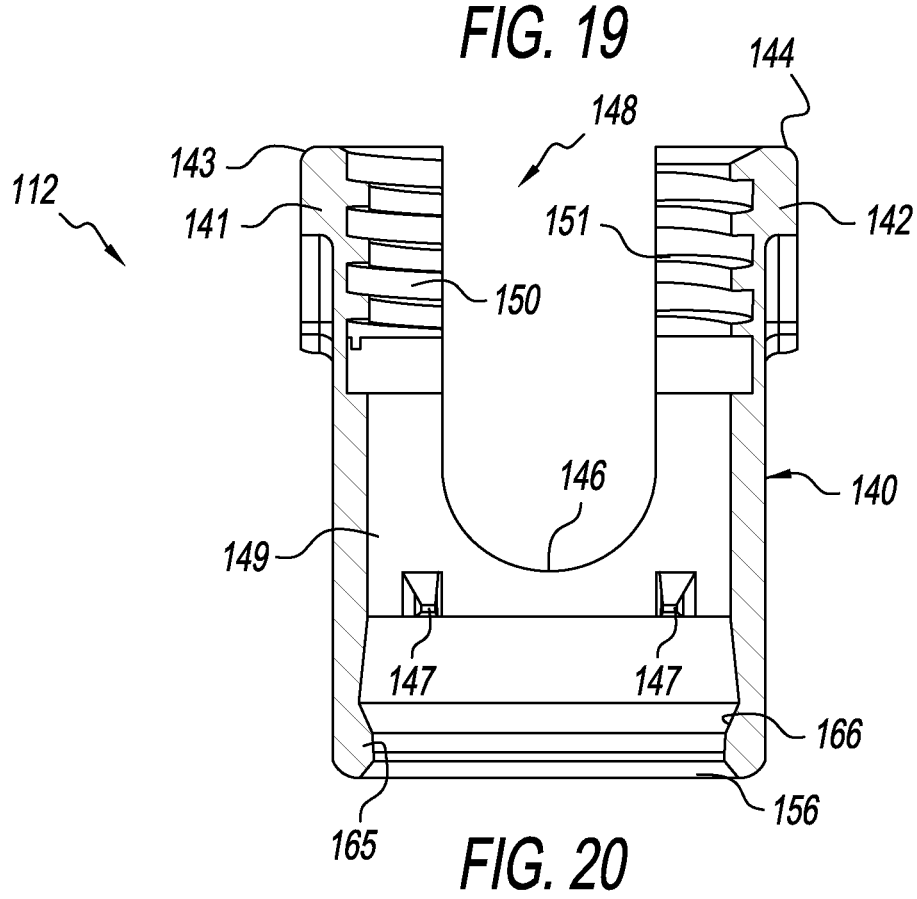
FIG. 20 is a sectional view of the tulip head of the modular poly-axial bone screw assembly of FIG. 11 taken long line 20-20 of FIG. 19.
Figure 21:
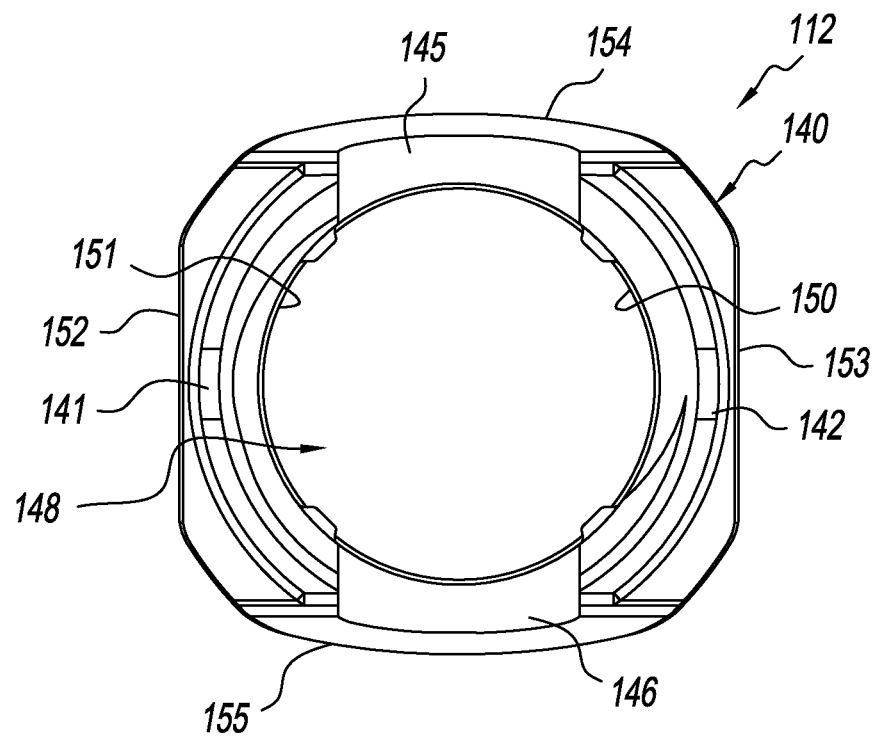
FIG. 21 is an enlarged top view of the tulip head of the modular poly-axial bone screw assembly of FIG. 11.

The inside of the tulip head 112 has an inner configuration best discerned in FIG. 17. Particularly, the inner configuration comprises a plurality of radially inwardly projecting protuberances 147 extending about the lower inner circumferential wall of the tulip head. While four (4) protuberances 147 are shown, any number may be used. Moreover, the configuration of the protuberances may be changed as necessary. The annular lower sidewall of the body 140 is preferably, but not necessarily, wider at the bottom 156.

The insert/collet 114 provides a taper lock and is defined by a generally cylindrical body 126 having a base or skirt 132 on a lower portion thereof, a first upstanding flange, side or sidewall 128, and a second upstanding flange, side or sidewall 129 that define a first pocket, cutout or notch 130 between lateral sides of the first and second upstanding flanges 128, 129, and a second pocket, cutout or notch 131 between opposite lateral sides of the first and second upstanding flanges 128, 129, the notches 130, 131 thus being oppositely disposed. The first and second notches 130, 131 are formed to receive a spine rod therein (not shown) and thus are generally arcuate or cup-shaped. An interior bore extends from a top of the body to a bottom 135 of the body. The bore allows access to the socket 124 of the bone screw head 122 of the poly-axial bone screw 116.

A bottom area 132 of the collet 114 includes a plurality of cuts, cutouts, notches or the like 133 that extend axially from the bottom 135 towards the upstanding flanges 128, 129. Each cut 133 is preferably, but not necessarily, equally circumferentially spaced about the bottom area 132 of the body 126 and terminates axially in a hole 134. The cuts 133 create a collet mechanism that allows the screw head 122 to snap into the bottom area 132 of the collet 114 thus creating a frictional interference fit. It should be appreciated that the number of cuts 133 may vary from two (2) to as many as desired. It is also preferable, but not necessary, that the cuts 133 are evenly spaced about the bottom area 132. The cuts 133 create a resilient or elastic interference or snap on fit with the polyaxial screw head 122 by allowing the bottom area 132 to splay slightly then form back around the screw head 122. The spherical coverage of the head 122 increases the amount of surface contact between the bottom area 132 of the collet 114 and the polyaxial screw head 122.

Figure 22:
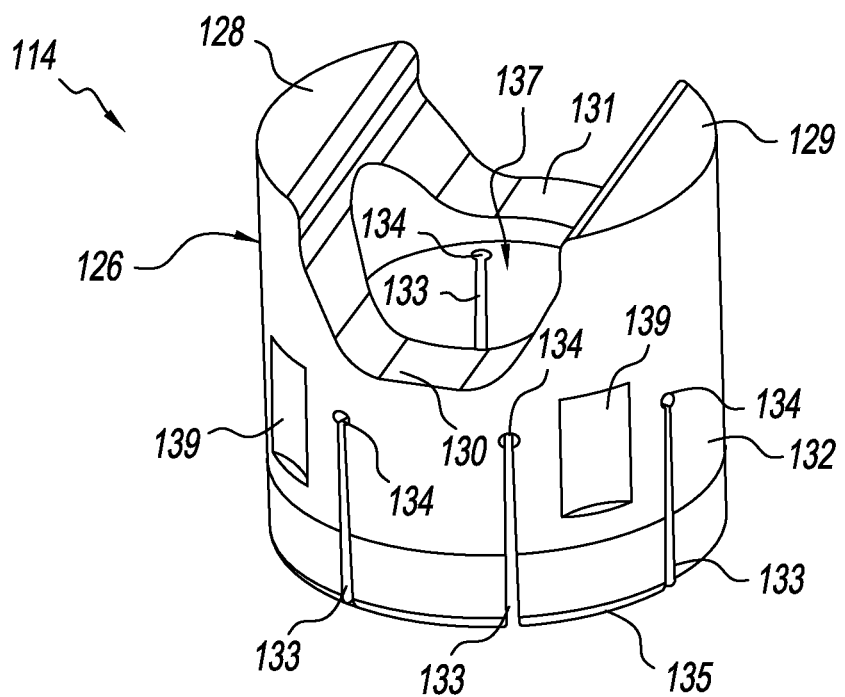
FIG. 22 is an isometric view of the collet of the modular poly-axial bone screw assembly of FIG. 11.
Figure 23:
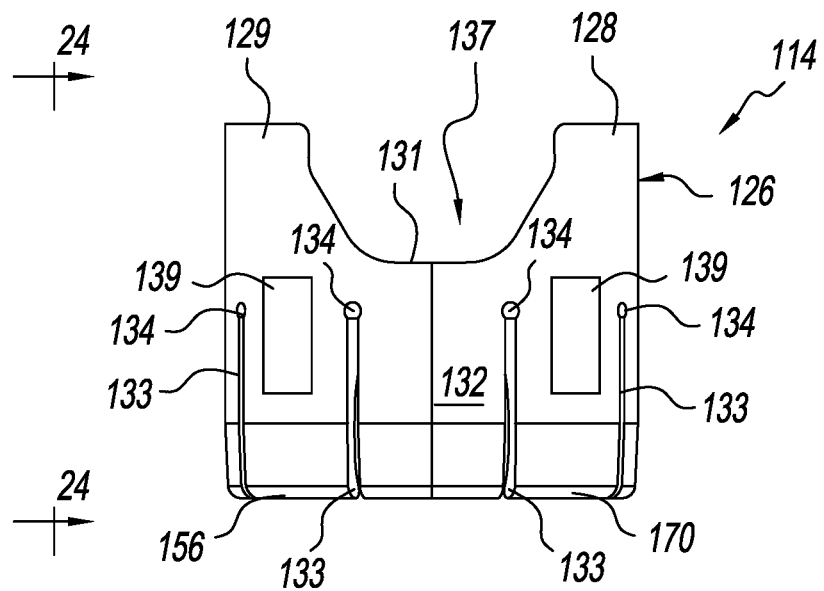
FIG. 23 is a side view of the collet of the modular poly-axial bone screw assembly of FIG. 11.
Figure 24:
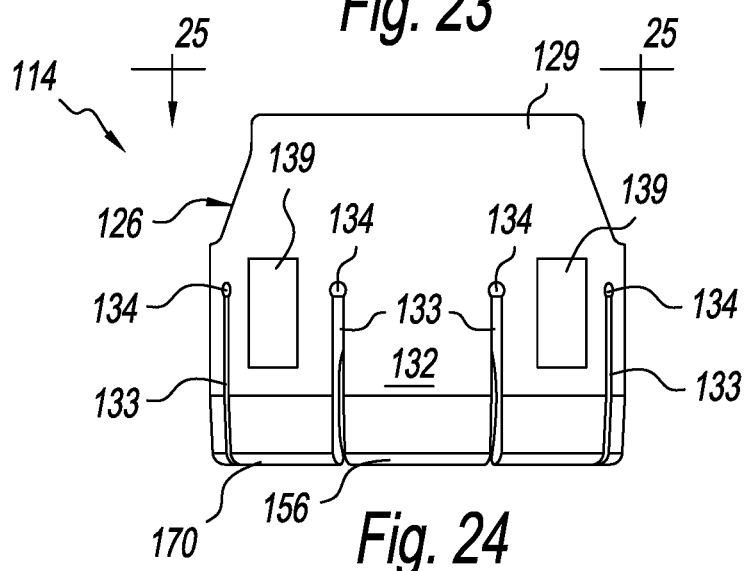
FIG. 24 is another side view of the collet of the modular poly-axial bone screw assembly of FIG. 11 taken along line 24-24 of FIG. 23.
Figure 25:
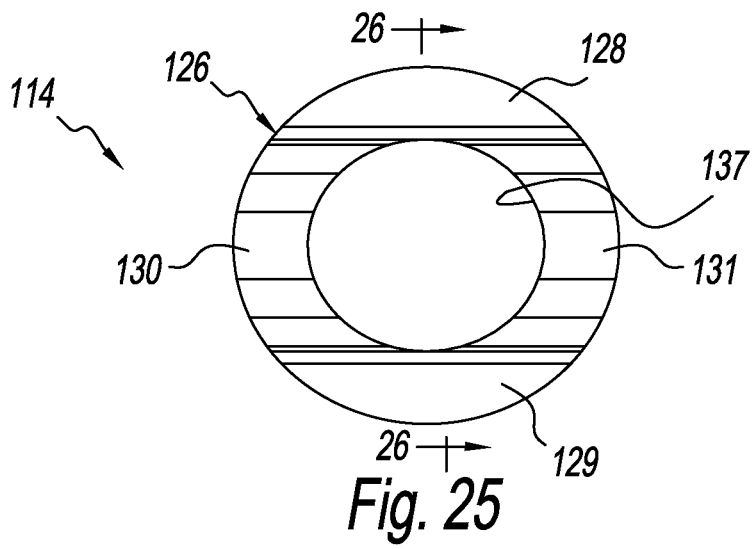
FIG. 25 is a top view of the collet of the modular poly-axial bone screw assembly of FIG. 11 taken along line 25-25 of FIG. 24.
Figure 26:
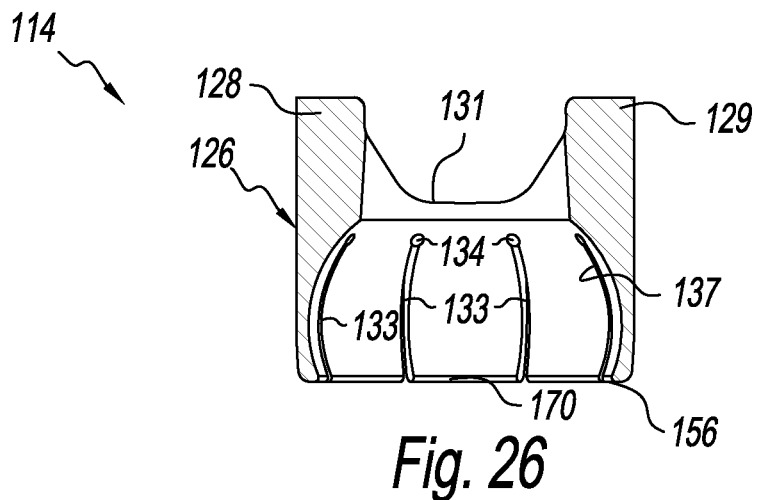
FIG. 26 is a sectional view of the collet of the modular poly-axial bone screw assembly of FIG. 11 taken along line 26-26 of FIG. 25.
Figure 27:
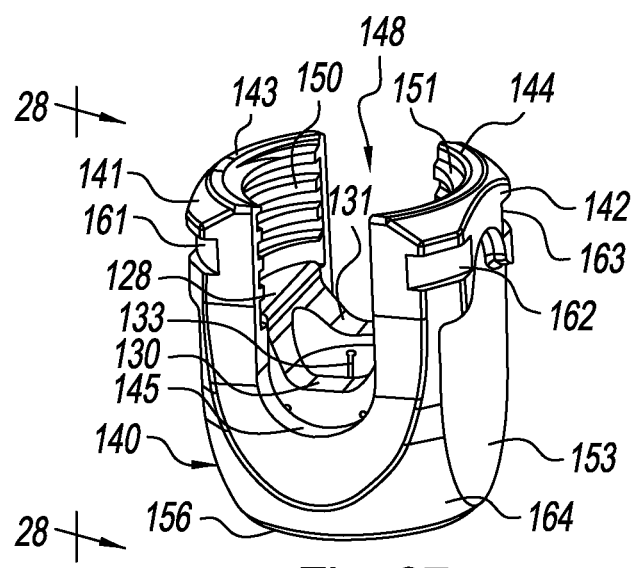
FIG. 27 is an isometric view of an assembly of the collet and tulip head of the modular poly-axial bone screw assembly of FIG. 11.
Figure 28:
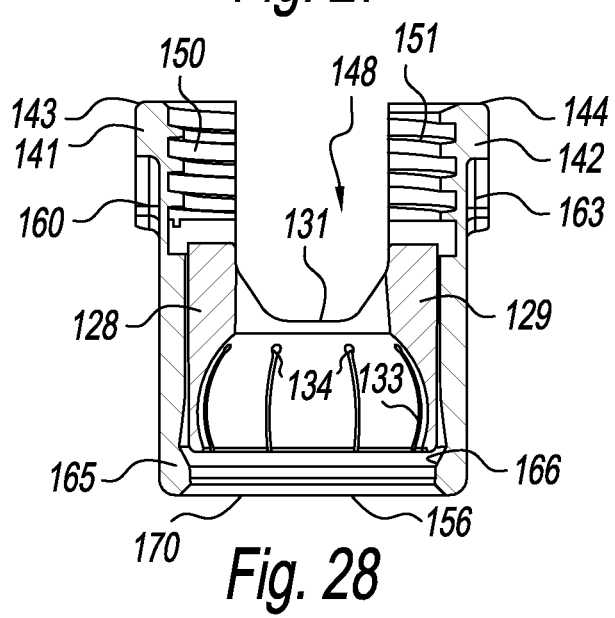
FIG. 28 is a section view of the collet and tulip head assembly of the modular poly-axial bone screw assembly of FIG. 11 taken along line 28-28 of FIG. 27.

The outside of the collet 114 has an outer configuration best discerned in FIG. 22. Particularly, the outer configuration comprises a plurality of depression, cutouts or the like 139 extending about the lower outer circumferential wall of the collet. The number of depressions 139 correspond in number to the plurality of protuberances 147 of the tulip head 112. While four (4) depressions 139 are shown, any number may be used. Moreover, the configuration of the depressions may be changed as necessary.

FIGS. 29-34 show cross-sectional views of the polyaxial bone screw assembly 100, according to various exemplary embodiments. During or prior to use of the polyaxial bone screw assembly 100, the collet 114 (shown in FIGS. 22-25) may be inserted within the tulip head 112 (e.g., via placement between the first sidewall 141 and the second sidewall 142 within the interior bore 148 of the body 120) to form a tulip head sub-assembly 171 (i.e., rod holder). As illustrated in the preceding FIGS. 28 and 29, the collet 114 is held in place within the tulip head 112 via engagement of the protuberances 147 of the tulip head 112 with each corresponding depressions 139 of the collet 114. After the collet 114 and the tulip head 112 have been mutually coupled forming the tulip head sub-assembly 171, the tulip head sub-assembly may then be coupled to the bone screw 116.

As shown in FIG. 29, which illustrates the polyaxial screw assembly 100 in a separated configuration, the tulip head sub-assembly 171 is positioned such that it is disposed a distance above the bone screw head 122 and aligned with a central, longitudinal axis 172 of the bone screw 116. As shown, an inner diameter of an edge along the bottom 135 of the collet 114 is smaller than an inner diameter of the area 132 and a maximum outer diameter of the bone screw head 122. Once positioned above the bone screw 116, the tulip head sub-assembly 171 is positioned atop the bone screw 116 such that the bottom 135 of the collet 114 and a bottom edge 170 of the tulip head 112 are in contact with the bone screw head 122, as shown in FIG. 30. The tulip head sub-assembly 171 is then be forced over the bone screw head 122 in response to a force applied to the tulip head 112 and/or the collet 114.

Figure 31:
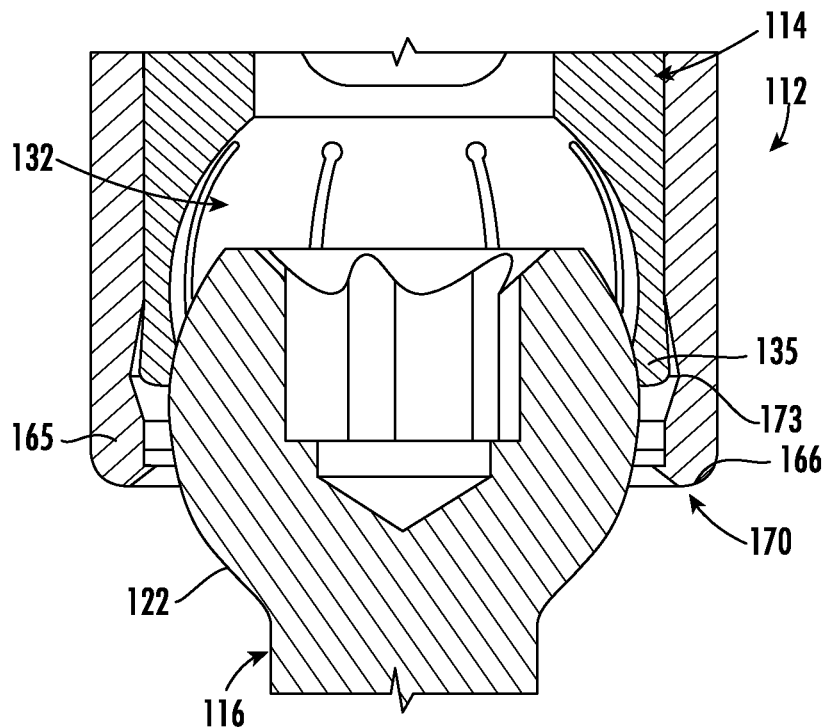
FIG. 31 is a cross-sectional view of the modular poly-axial bone screw assembly of FIG. 29 taken along line 28-28 of FIG. 27, wherein the collet and tulip head assembly is in another intermediate configuration.
Figure 32:
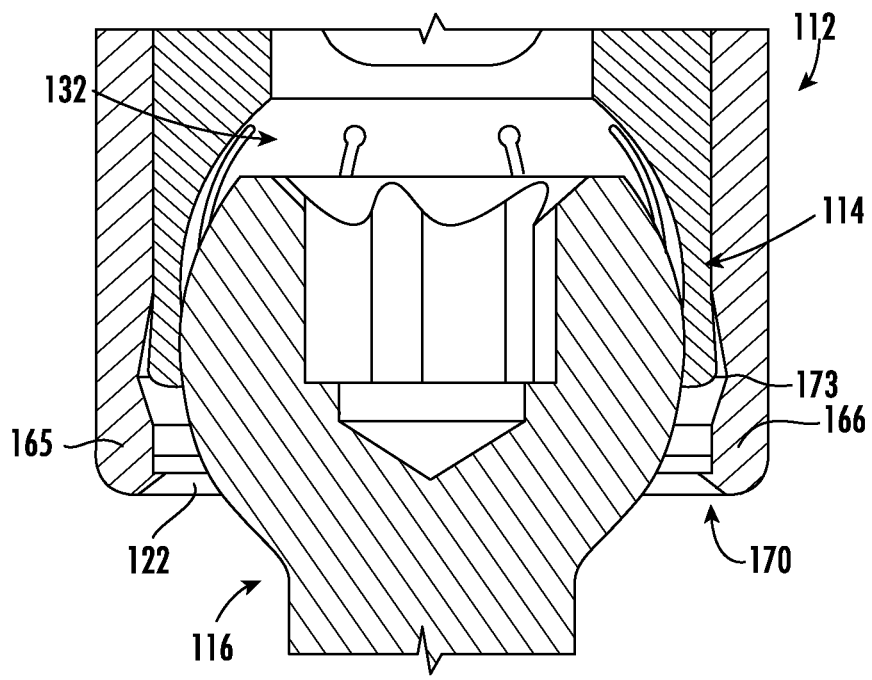
FIG. 32 is a cross-sectional view of the modular poly-axial bone screw assembly of FIG. 29 taken along line 28-28 of FIG. 27, wherein the collet and tulip head assembly is in yet another intermediate configuration.
Figure 33:
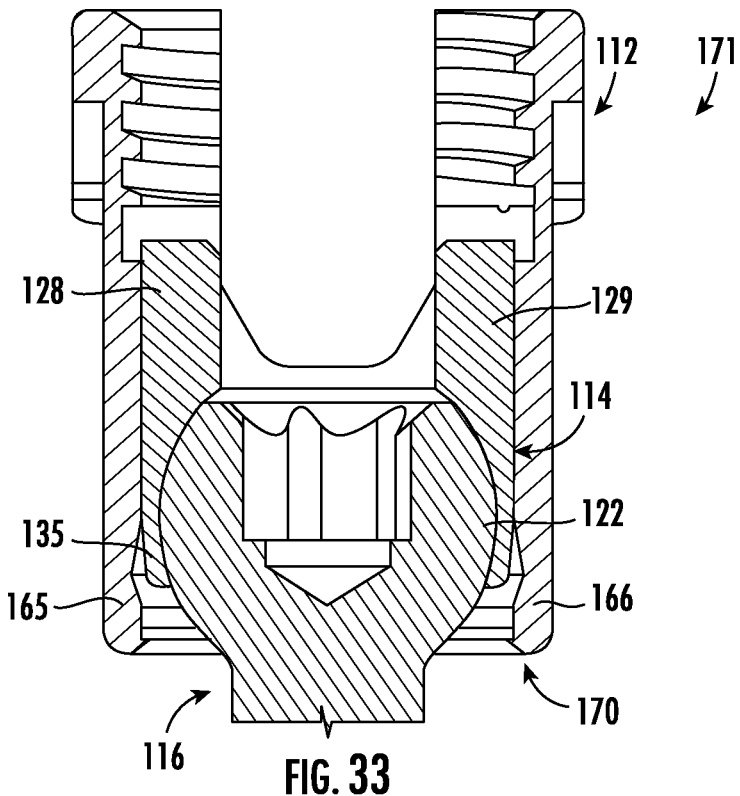
FIG. 33 is a cross-sectional view of the modular poly-axial bone screw assembly of FIG. 29 taken along line 28-28 of FIG. 27, wherein the collet and tulip head assembly is in a near-assembled configuration.
Figure 34:
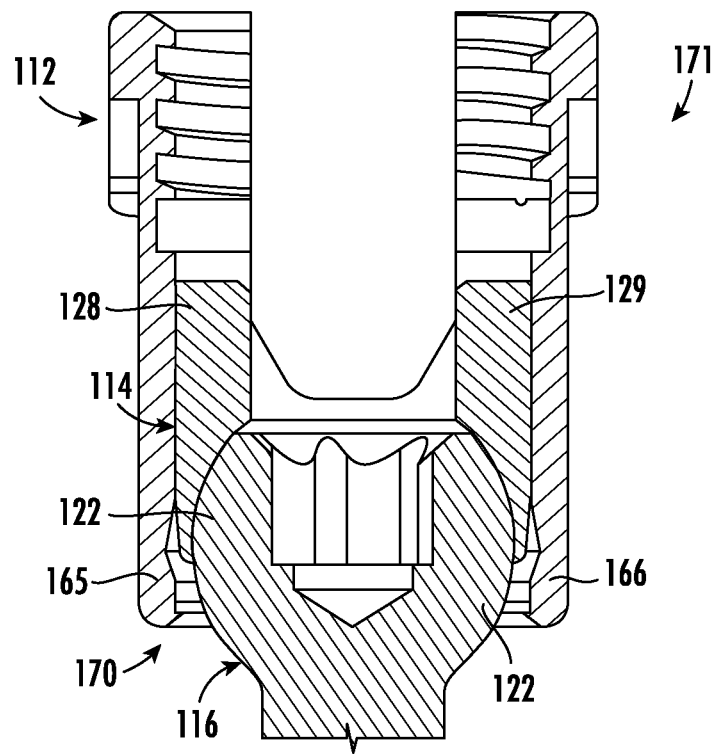
FIG. 34 is a cross-sectional view of the modular poly-axial bone screw assembly of FIG. 29 taken along line 28-28 of FIG. 27, wherein the collet and tulip head assembly is in an assembled configuration.

As illustrated in FIG. 31, the tulip head sub-assembly 171 engages with the bone screw head 122 in an intermediate configuration via the taper lock of the collet 114. As illustrated, the bottom area 132 of the collet 114 expands or splay to increase the interior diameter of the bottom 135. The expanded bottom 135 of the body 126 of the collet 114 is accommodated within a recessed region or relief 173 of the tulip head 112. Accordingly, when expanded, the bottom area 132 of the collet 114 receives the screw head 122 as the sub-assembly 171 moves vertically downward (per the orientation shown in the drawing) in response to an applied load. Once the sub-assembly 171 has been vertically displaced such that a portion of the bone screw head 122 having the maximum outer diameter is at least partially disposed within the bottom area 132 of the collet 114 (as shown in FIG. 32), the bottom 135 of the collet 114 advances past the relief 173 within the tulip head 112, contracting such that the inner diameter of the bottom 135 is again smaller than a maximum outer diameter of the bone screw head 122. The sub-assembly 171 may be displaced further such that the polyaxial modular bone screw assembly 100 is in an assembled configuration, as shown in FIG. 34. As illustrated, the bottom 135 of the collet 114 rests on a ridge having an inner diameter smaller than an inner diameter of the relief 173, and defined by one or more protuberances 165 and 166 disposed along a lower edge 170 (e.g., along or within the bottom 156) of the tulip head 112. Once the modular polyaxial bone screw assembly 100 is in the assembled configuration, the sub-assembly 171 is locked on the bone screw head 112 (facilitated by the taper lock of the collet 114).

In various embodiments, the displacement and subsequent engagement of the tulip head sub-assembly 171 with the bone screw 116 may facilitated by a locking cap and/or rod, which may be configured to engage with the collet 114 and/or tulip head 112. In various embodiments, a force may be applied to the locking cap and/or rod to cause displacement of the tulip head sub-assembly 171 and subsequent engagement with the bone screw 116.

Figure 36:
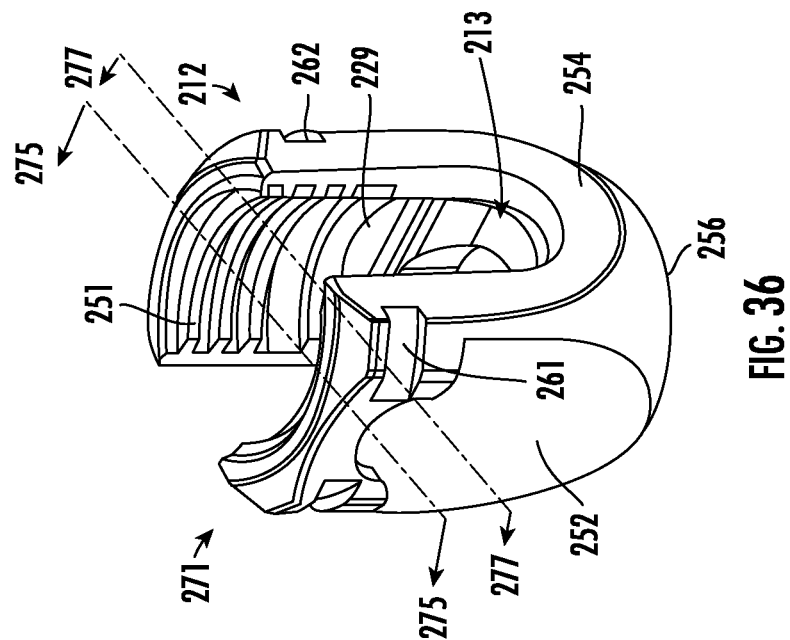
FIG. 36 is a perspective view of the collet and tulip head assembly of the modular poly-axial bone screw of FIG. 35.
Figure 35:
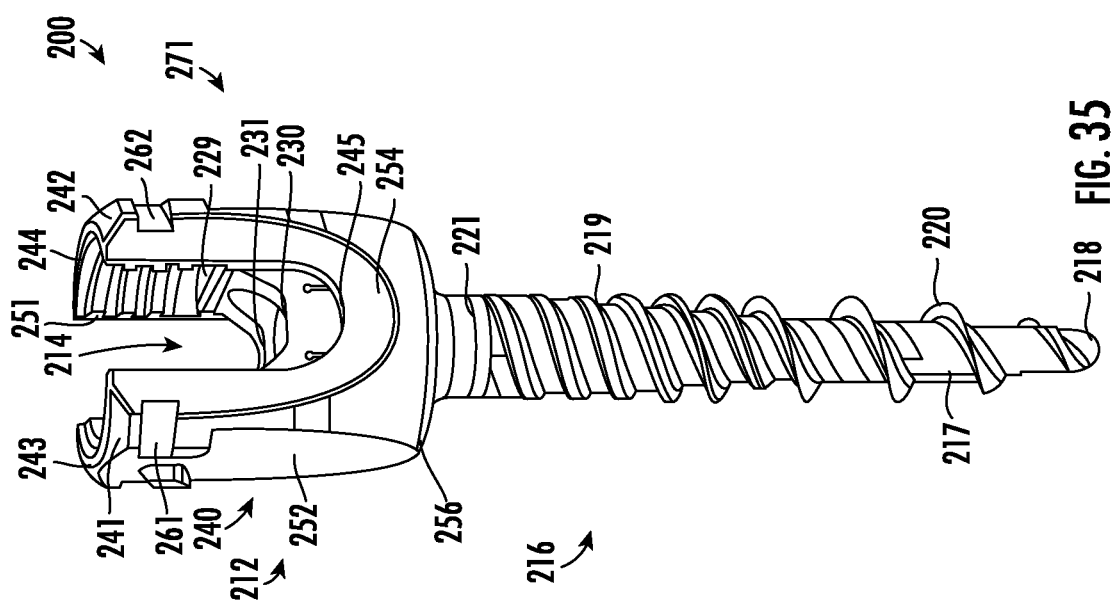
FIG. 35 is a perspective view of a modular poly-axial bone screw assembly, according to an exemplary embodiment.

FIG. 35 shows a perspective view of a modular polyaxial bone screw assembly 200, according to an exemplary embodiment. In various embodiments, elements 212 through 273 of the modular polyaxial bone screw assembly 200 are the same or equivalent to corresponding elements 112 through 173 of the modular polyaxial bone screw assembly 100. As shown in FIG. 35, the modular polyaxial bone screw assembly 200 includes a tulip head sub-assembly 271 (e.g., rod holder), which includes a collet 214 coupled within a tulip head 212, and which is configured to receive and be coupled to a bone screw 216 (e.g., via the bone screw head 222). FIG. 36, which shows a perspective view of the tulip head sub-assembly 271, further illustrates relative positioning of the collet 214 within the tulip head 212.

Figure 38:
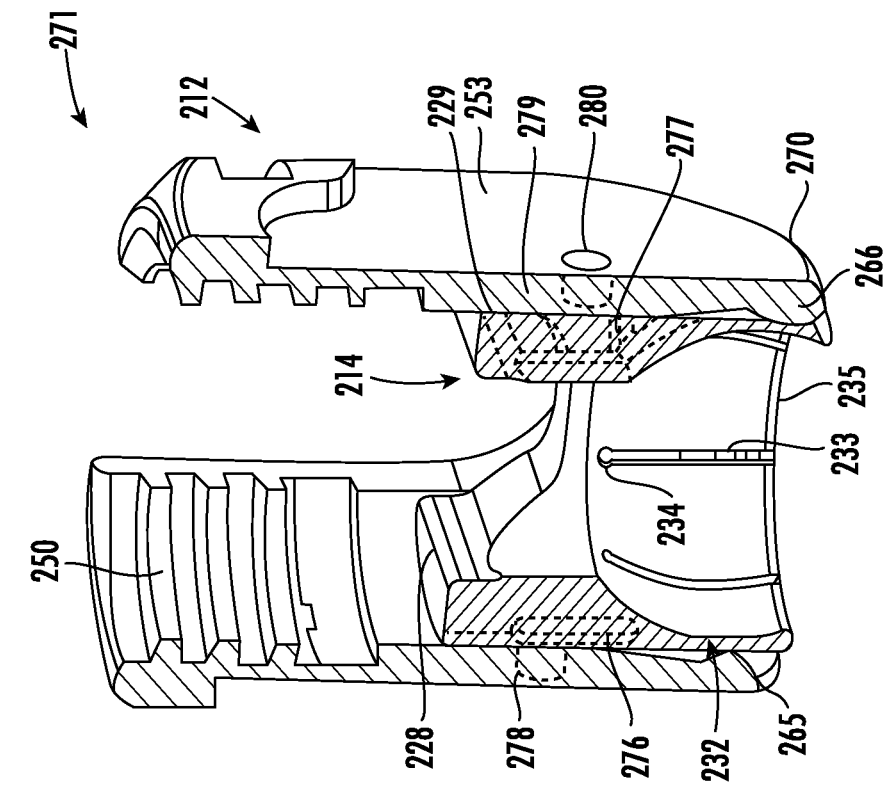
FIG. 38 is a perspective cross-sectional view of the collet and tulip head assembly of FIG. 36 taken along line 277-277 of FIG. 36.
Figure 37:
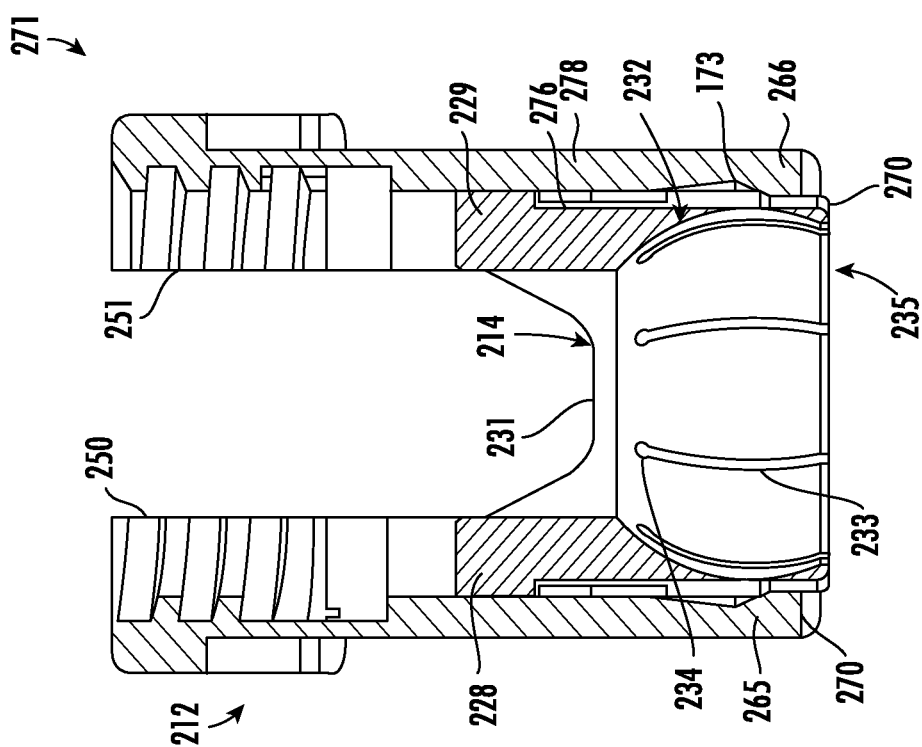
FIG. 37 is a front cross-sectional view of the collet and tulip head assembly of FIG. 35 taken along line 275-275 of FIG. 36.

FIG. 37 shows a front cross-sectional view of the tulip head sub-assembly 271 taken along line 275-275 of FIG. 36. As shown, the collet 214 includes one or more recessed channels 276 disposed within an outer surface of each of the sidewalls 228 and 229. The recessed channels 276 is configured to engage with one or more cross-pins 278, which extends from an inner surface of the tulip head 212. FIG. 38, which shows a perspective cross-sectional view of the tulip head sub-assembly 271 taken along line 277-277 of FIG. 36, further illustrates a disposition of the recessed channels 276 relative to the cross-pins 278. In various embodiments, when the collet 214 is being inserted within the tulip head 212 for coupling, the cross-pins 278 of the tulip head 212 engage with the channels 276 of the collet 214. Accordingly, the engagement of the channels 276 with the cross-pins 278 prevent separation of the collet 214 from the tulip head 212. In various embodiments, the channels 276 may have a length greater than a width or diameter of the cross-pins 278 such that the channels 276 allow for limited vertical displacement of the collet 214 within the tulip head 212 (per the orientation shown in the drawing). In various embodiments, the cross-pins 278 may be coupled to or integrally formed within the tulip head 212. In various embodiments, the cross-pins 278 may have circular, ellipsoidal, or polygonal cross-sections.

Figure 39:
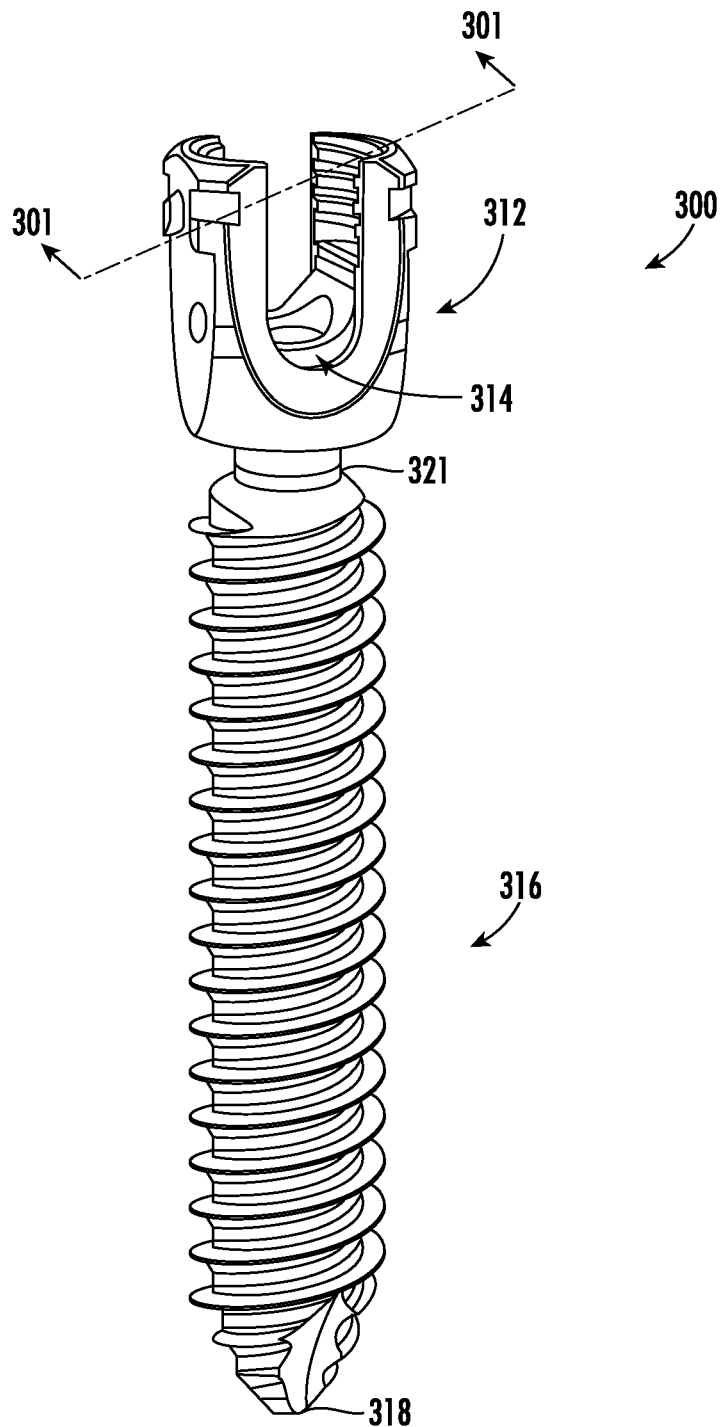
FIG. 39 is a perspective view of a modular poly-axial bone screw assembly, according to an exemplary embodiment.
Figure 40:
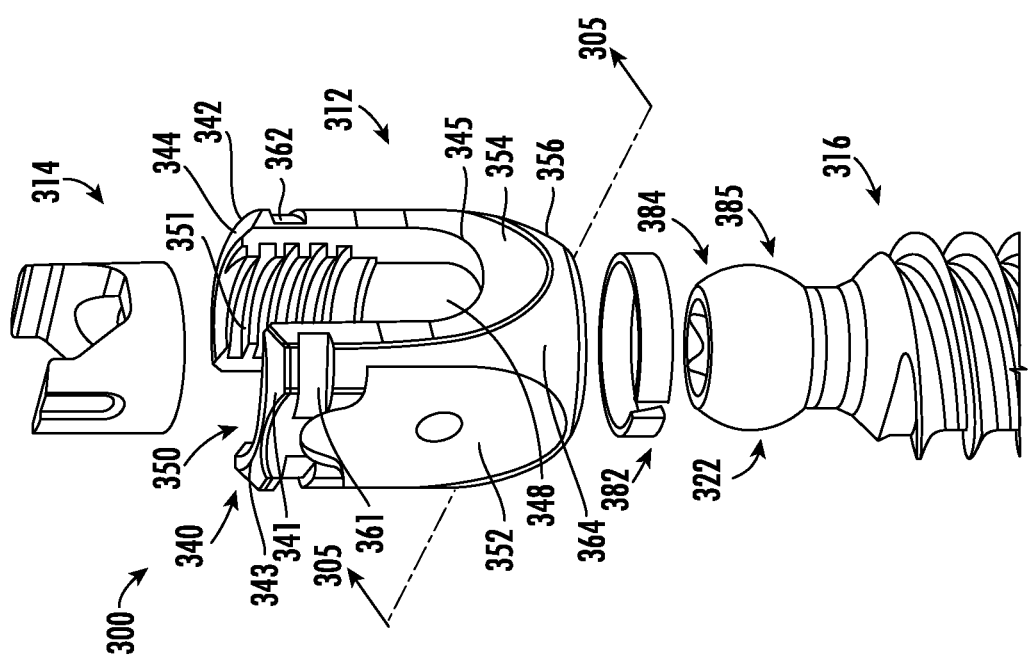
FIG. 40 is a perspective exploded view of the modular poly-axial bone screw assembly of FIG. 39.

FIGS. 39 and 40 shows a perspective and exploded views, respectively, of a modular polyaxial bone screw assembly 300, according to an exemplary embodiment. In various embodiments, the modular poly-axial bone screw 300 is configured for holding a spine rod (not shown) relative to the spine (not shown). In like form as the modular poly-axial bone screw 10, 100, 200, the modular poly-axial bone screw 300 includes three components, namely a bone screw 316 (similar or equivalent in configuration and/or function as bone screws 16, 116, 216), a tulip head 312 (similar or equivalent in configuration and/or function as tulip heads 12, 112, 212), and collet 314 (similar or equivalent in configuration and/or function as collets 14, 114, 214). As shown in FIG. 40, the modular polyaxial bone screw assembly 300 further includes a clip (shown as a "c-clip" 382).

The tulip head 312 ("rod holder") may be defined by a generally tulip shaped body 340, having a bottom 356, a first sidewall 341 and a second sidewall 342, the second sidewall 342 opposite the first sidewall 341, the nomenclature first and second being arbitrary here and throughout unless otherwise indicated. The first sidewall 341 is generally arc-shaped and includes one or more threads/threading 350 on its interior wall/surface. The second sidewall 342 is generally arc-shaped and includes threads/threading 351 on its interior wall/surface. The internal threading 350, 351 is configured to accept a set screw (not shown) for fully seating the spine rod in the tulip head 312. The first sidewall 341 has an arcuate top 343 that is preferably, but not necessarily, sloped or slanted radially inwardly, and the second sidewall 341 likewise has an arcuate top 344 that is preferably, but not necessarily, sloped or slanted radially inwardly. Each of the first sidewall 341 and second sidewall includes a flat 352 on each respective exterior surface extending generally from proximate the respective top 343 and 344 to the bottom 356. The first sidewall 341 further includes notches 361 disposed on opposing lateral sides of the sidewall 341 proximate the top 143, the first and second notches permitting receipt of an installation tool and otherwise. Similarly, the second sidewall 342 includes a notches 362 on opposing lateral sides of the sidewall 342 proximate the top 344. A lower portion 364 of the tulip head 312 body 340 may be generally round in shape.

As shown in FIG. 40, the tulip head 312 includes an inner bore 348, which extends from the tops 343 and 344 of first and second sidewalls 341 and 342, respectively, to the bottom 356 of the tulip head 312 body 340. The bore 348 is configured to receive the bone screw 316 and the collet 314. A spine rod reception area is defined in the body 340, the reception area formed by pockets, cutouts or notches 345, which are disposed between opposite lateral sides of the first sidewall 341 and the second sidewall 342. The notches 345 are configured to receive a spine rod therein (not shown) and thus may be generally arcuate or cup-shaped. A portion of the body 340 of the tulip head 312 surrounding each of the notches 345 comprises a flat 354. In various embodiments, the threading 350, 351 of the corresponding first and second sidewalls 341, 342, provide for reception of a set screw or the like (not shown) that may be used to secure the tulip head 312 on and relative to the bone screw 316 via the collet 314.

Figure 41:
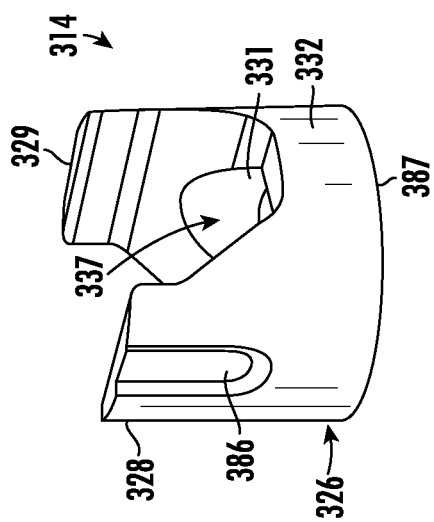
FIG. 41 is a perspective view of the collet of the modular poly-axial bone screw assembly of FIG. 39.

FIG. 41, shows a perspective view of the collet 314 of the modular polyaxial bone screw assembly 300. As shown, the collet 314 is defined by a generally cylindrical body 326 having a base 332 on a lower portion thereof, a first upstanding flange, side or sidewall 328, and a second upstanding flange, side or sidewall 329 that define pockets, cutouts or notches 331 between opposite lateral sides of the first and second upstanding sidewalls 328, 329. In various embodiments, the first and second notches 331 are formed to receive a spine rod therein (not shown) and thus are generally arcuate or cup-shaped. An interior bore 337 extends from a top of the body to a bottom 387 of the body. In various embodiments, the bore 337 may allow for access to the socket of the bone screw head 322 of the polyaxial bone screw 316. As illustrated in FIG. 41, each of the sidewalls 328, 329 may include a vertically aligned channel 386, which may terminate in a rounded end. In various embodiments, each of the channels 386 are configured to slidably engage with one or more protruding features of the tulip head 312 to facilitate alignment and/or securing therein. In various embodiments, an interior region of the base 332 of the collet 314 is shaped to conform to an outer surface contour of a top portion 384 of the bone screw head 322. In various embodiments, the base 332 of the collet 314 is configured for positioning upon the top portion 384 of the bone screw head 322.

Figure 42:
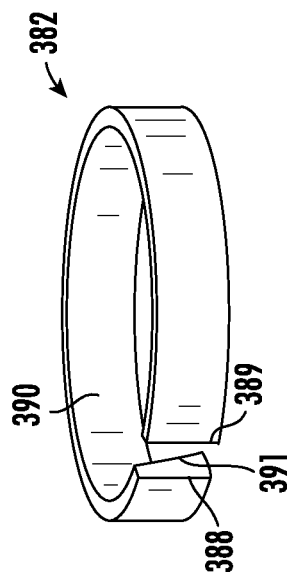
FIG. 42 is a perspective view of the c-clip of the modular poly-axial bone screw assembly of FIG. 39.

FIG. 42 shows a perspective view of the c-clip 382 of the modular polyaxial bone screw assembly 300. As shown, the c-clip 382 includes a substantially circular ring that forms a "c" shape terminating in first and second ends 388 and 389 respectively. The c-clip 382 is configured to couple to and/or form an interference fit with a bottom portion 385 of the bone screw head 322 to facilitate further coupling of the bone screw 316 to the tulip head 312. As shown in FIG. 42, the c-clip 382 includes a gap disposed between the first and second ends 388 and 389. In various embodiments, an inner diameter of the c-clip 382 is smaller than an outer diameter of the bottom portion 385 of the bone screw head 322. Accordingly, the c-clip 382 is configured to elastically flex such that the gap between the first and second ends 388 and 389 increases to enable placement of the c-clip 382 about an outer surface of the bottom portion 385 of the bone screw head 322 to form an interference fit therebetween. In various embodiments, an inner surface 390 of the c-clip 382 is rounded so as to conform to a contour of the bottom portion 385 of the bone screw head 322. In various embodiments, a bottom edge of the c-clip 382 includes a ledge or lip 391 to prevent downward displacement of the bone screw head 322 relative to the c-clip 382. In other embodiments, the clip may have other shapes and configurations designed to accommodate the contours of the bone screw head or tulip head.

Figure 44:
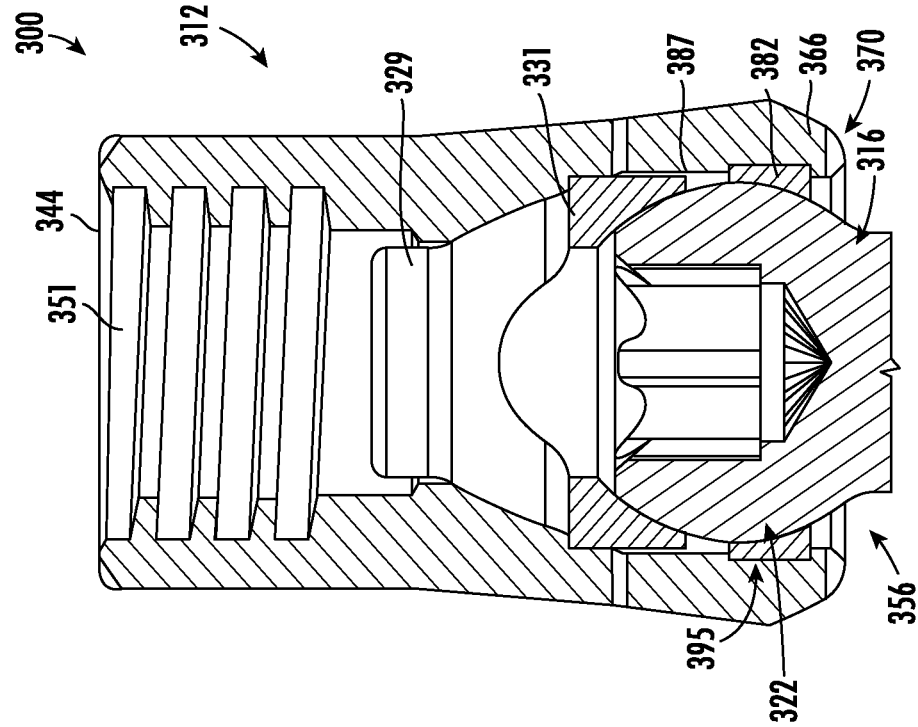
FIG. 44 is a side cross-sectional view of the collet and tulip head assembly of FIG. 39 taken along line 305-305 of FIG. 40.
Figure 43:
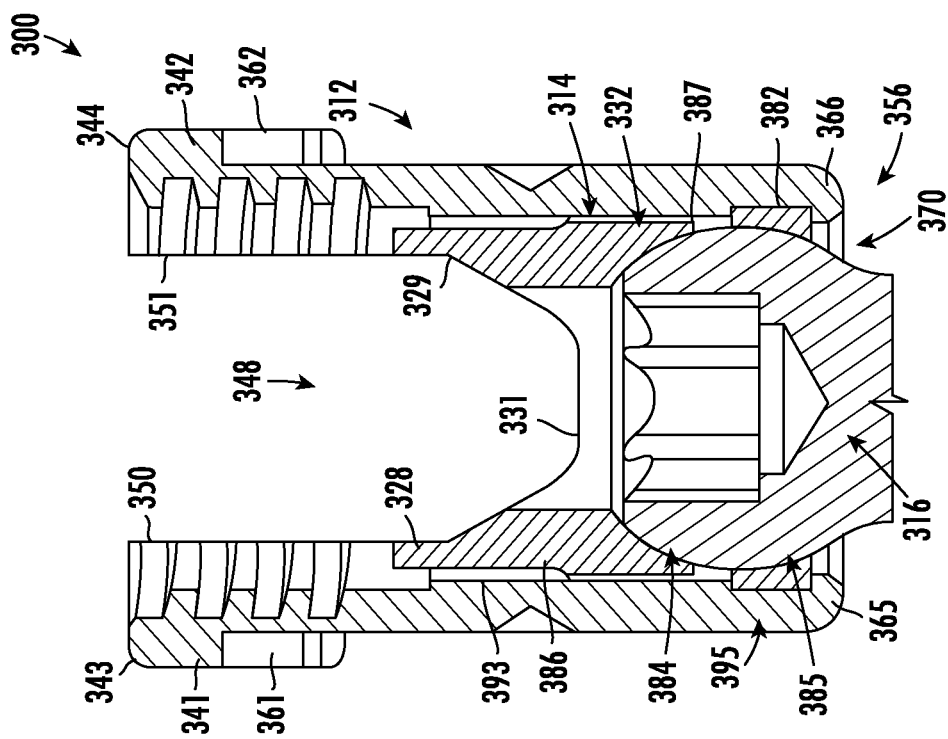
FIG. 43 is a front cross-sectional view of the collet and tulip head assembly of the modular poly-axial bone screw assembly of FIG. 39 taken along line 301-301 of FIG. 39.

FIGS. 43 and 44 show alternate cross-sectional views of the modular polyaxial bone screw assembly 300 taken along line 301-301 of FIG. 39 and along line 305-305 of FIG. 40, respectively. As illustrated in FIGS. 43 and 44, the collet 314 may be configured to fit within the tulip head 312. As shown, the first and second upstanding sidewalls 328 and 329 of the collet 314 may be aligned with the first and second sidewalls 341 and 342 of the tulip head 312, respectively. Furthermore, the vertically aligned channels 386 disposed within each of the first and second upstanding sidewalls 328 and 328 may be configured to engage with corresponding protruding portions 393, which may be disposed along an inside surface of each of the first and second sidewalls 341 and 342 of the tulip head 312. In various embodiments, the protruding portions 393 may comprise a longitudinal ridge extending along an interior length of each of the first and second sidewalls 341 and 342. In various embodiments, the protruding portions 393 may comprise one or more pins, pegs, knobs, or other protruding components. Accordingly, when the collet 314 is inserted within the bore 348 of the tulip head 312, the base 332 of the collet 314 may be fitted to the top portion 384 of the bone screw head 322 and held in place via the engagement of the channels 386 with the corresponding protruding portions 393 of the tulip head 312.

As shown, the c-clip 382 is accommodated within the tulip head 312. In various embodiments, the c-clip 382 is disposed within a recess or relief 395 (e.g., notch, groove, track, etc.) disposed within or near the bottom 356 of the tulip head 312. In various embodiments, the recess or relief 395 is configured to be larger than the c-clip 382 (e.g., in diameter, width, depth, etc.) to accommodate expansion of the c-clip 382 upon insertion of the bone screw head 322 into the tulip head 312 during assembly of the modular polyaxial bone screw assembly 300. The c-clip 382 may be retained within the tulip head 312 by a ridge or lip formed by one or more protruding features 365 and 366 disposed at or near a bottom edge 370 (e.g., along or within the bottom 356) of the tulip head 312.

In various embodiments, the coupled c-clip 382 and tulip head 312 may be further coupled to the bone screw head 322. To facilitate coupling of the bone screw head 322, the bone screw 316 may be inserted or threaded through the bottom 356 of the tulip head 312 (e.g., through the bore 348). Accordingly, the c-clip 382 may expand about the bottom portion 385 of the bone screw head 322 when a force is applied to the tulip head 312 or the bone screw 316, which causes the bone screw head 322 to displace into the bottom portion of the tulip head. Once the c-clip 382 is coupled to the bone screw head 322, the collet 314 may be inserted into the central bore 348 of the tulip head 312. The protruding portions 393 of the tulip head 312 may engage within the channels 386 of the collet 314 to retain the collet 314 within the tulip head 312. In various embodiments, the collet 314 and/or the tulip head 312 may include fewer or additional engaging features to retain the collet 314 within the tulip head 312.

In various embodiments, the c-clip 382 and the tulip head 312 may comprise a pre-assembled portion of the modular polyaxial bone screw assembly 300 such that the c-clip 382 may be coupled to the tulip head 312 after manufacture and prior to distribution or use of the assembly 300. In various embodiments, the modular polyaxial bone screw assembly 300 may be configured as a one-way assembly, such that the components of the assembly 300 may not be separated after coupling.

The various components of the modular poly-axial bone screw assemblies 10, 100, 200, 300 are made from a bio-compatible material such as, but not limited to, PEEK, other polymers/plastics, titanium, stainless steel, and alloys of same. Other bio-compatible materials, or course, may be used.

While the invention has been illustrated and described in detail in the drawings and foregoing description, the same is to be considered as illustrative and not restrictive in character, it being understood that only preferred forms have been shown and described and that all changes and modifications that come within the spirit of the invention are desired to be protected.

Notwithstanding the embodiments described above in FIGS. 1-44, various modifications and inclusions to those embodiments are contemplated and considered within the scope of the present disclosure.

It is also to be understood that the construction and arrangement of the elements of the systems and methods as shown in the representative embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. Also, use of directional terms are referenced in view of the drawings and not necessarily in any actual application or performance of the disclosed structure or processes.

Accordingly, all such modifications are intended to be included within the scope of the present disclosure. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other illustrative embodiments without departing from scope of the present disclosure or from the scope of the appended claims.

Furthermore, functions and procedures described above may be performed by specialized equipment designed to perform the particular functions and procedures. The functions may also be performed by general-use equipment that executes commands related to the functions and procedures, or each function and procedure may be performed by a different piece of equipment with one piece of equipment serving as control or with a separate control device.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Similarly, unless otherwise specified, the phrase "based on" should not be construed in a limiting manner and thus should be understood as "based at least in part on." Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

Moreover, although the figures show a specific order of method operations, the order of the operations may differ from what is depicted. Also, two or more operations may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection operations, processing operations, comparison operations, and decision operations

What is claimed is:

1. A modular bone screw assembly for holding a spine rod in a fixed spatial orientation relative to vertebral bone, the modular bone screw assembly comprising:
   a bone screw having a threaded shank and a screw head;
   a tulip head disposed on the screw head and configured to move relative to the screw head before the tulip head is fixed in spatial orientation relative to the bone screw, and configured to receive and hold the spine rod as the spatial orientation of the tulip head is fixed, the tulip head having a bore extending from a first end of the tulip head to a second end of the tulip head and having an upper portion, inner threading for threaded receipt of a set screw, a lower portion sized to receive the screw head, and one or more protruding members extending from an inner surface of the bore;
   a collet disposed within the bore of the tulip head, the collet having a lower section of a first diameter with a first end configured to rest upon a top portion of the screw head, the collet having one or more engagement members disposed along an exterior portion of the collet; and
   an elastically deforming c-clip configured for coupling to the bone screw, wherein the c-clip is retained within a lower portion of the tulip head;
   wherein the one or more engagement members of the collet are configured to engage with the corresponding one or more protruding members extending from the inner surface of the bore.

2. The modular bone screw assembly of claim 1, wherein the c-clip has a second diameter and the screw head has a third diameter, the third diameter being larger than each of the first diameter and the second diameter.

3. The modular bone screw assembly of claim 1, wherein the c-clip is configured to elastically deform to receive a bottom portion of the screw head and form an interference fit therewith.

4. The modular bone screw assembly of claim 3, wherein an interior surface of the c-clip is shaped to conform to a contour of the bottom portion of the screw head.

5. The modular bone screw assembly of claim 1, wherein the c-clip is retained and expandable within a recess disposed within the lower portion of the tulip head.

6. The modular bone screw assembly of claim 5, wherein the tulip head comprises a ledge disposed at a bottom edge of the tulip head, wherein the ledge is configured to retain the c-clip within the recess.

7. The modular bone screw assembly of claim 1, wherein the one or more engagement members are configured as one or more channels extending along a length of the collet.

8. The modular bone screw assembly of claim 7, wherein the one or more protruding members of the tulip head are configured as longitudinal ridges extending along opposing surfaces within the interior of the tulip head, and wherein the one or more protruding members are configured to slidably engage with the one or more channels of the collet.

9. The modular bone screw assembly of claim 7, wherein the one or more protruding members of the tulip head are configured as a plurality of radially inwardly projecting protuberances extending from opposing surfaces within the interior of the tulip head, and wherein the one or more protruding members are configured to slidably engage with the one or more channels of the collet.

10. A method for assembling a modular polyaxial bone screw assembly, the method comprising:
   inserting a collet into a central bore of a tulip head such that an exterior of the collet is accommodated by an interior of the tulip head;
   inserting a bone screw through the central bore of the tulip head such that a bottom portion of a screw head of the bone screw is received within a lower portion of the tulip head;
   applying a force to at least one of the bone screw or the tulip head such that the screw head is displaced into the lower portion of the tulip head; and
   wherein:
      the bone screw includes a threaded shank, which extends from the screw head;
      the tulip head is disposed on the screw head and configured to move relative to the screw head before the tulip head is fixed in spatial orientation relative to the bone screw, and configured to receive and hold a spine rod as the spatial orientation of the tulip head is fixed;
      the central bore of the tulip head extends from a first end of the tulip head to a second end of the tulip head and includes an upper portion and inner threading for threaded receipt of a set screw, and wherein the lower portion is sized to receive the screw head in its entirety, and one or more protruding members extending from an inner surface of the central bore; and
      the collet is disposed in the interior of the tulip head, the collet having a lower section of a first diameter with a first end configured to rest upon a top portion of the screw head, the collet having one or more engagement members disposed along an exterior portion of the collet, and wherein the one or more engagement members of the collet are configured to engage with the corresponding one or more protruding members disposed within the interior of the tulip head.

11. The method of claim 10, further comprising: inserting an elastically deformable c-clip within the lower portion of a tulip head such that the c-clip is aligned with the central bore of the tulip head.

12. The method of claim 11, wherein the c-clip is configured for coupling to the bone screw, wherein the c-clip is retained within the lower portion of the tulip head.

13. The method of claim 12, wherein an interior surface of the c-clip is shaped to conform to a contour of the bottom portion of the screw head.

14. The method of claim 11, wherein the c-clip is configured to elastically deform such that an inner surface of the c-clip receives a bottom portion of the screw head and forms an interference fit therewith.

15. A method for assembling a modular polyaxial bone screw assembly, the method comprising:
  inserting a collet into a central bore of a tulip head such that an exterior of the collet is accommodated by an interior of the tulip head;
  positioning the collet and the tulip head adjacent a top portion of a screw head of a bone screw, such that a central axis of the central bore is aligned with a central axis of the bone screw;
  applying a force to at least one of the collet and the tulip head such that the collet and the tulip head are displaced relative to the bone screw, wherein the bone screw is received within a lower portion of the tulip head;
  wherein:
    the bone screw includes a threaded shank, which extends from the screw head;
    the tulip head is disposed on the screw head and configured to move relative to the screw head before the tulip head is fixed in spatial orientation relative to the bone screw, and configured to receive and hold a spine rod as the spatial orientation of the tulip head is fixed;
    the central bore of the tulip head extends from a first end of the tulip head to a second end of the tulip head and includes an upper portion and inner threading for threaded receipt of a set screw, and wherein the lower portion is sized to receive the screw head in its entirety;
    the collet is disposed in the interior of the tulip head, the collet having a lower section of a first diameter with a first end configured to rest about the top portion of the screw head, and an upper section of a second diameter that is smaller than the first diameter of the lower section, wherein the collet is configured to splay on the screw head and fix the spatial orientation of the tulip head relative to the bone screw through interference between the first end, the screw head, and the tulip head responsive to the bone screw being received within the lower portion of the tulip head,
  wherein inserting the collet into the central bore of the tulip head comprises engaging one or more protuberances of at least one of the collet or the tulip head with one or more recesses of the other of the at least one of the collet or the tulip head.

16. The method of claim 15, wherein the lower section of the collet includes a plurality of cutouts configured to enable splaying of the collet about the screw head.

17. The method of claim 16, wherein the collet includes the one or more recesses, the one or more recesses disposed radially about an exterior portion of the collet.

18. The method of claim 17, wherein the tulip head comprises the one or more protuberances, the one or more protuberances configured to engage with each of the one or more recesses of the collet.

19. The method of claim 18, wherein inserting the collet into the central bore of the tulip head comprises engaging the one or more protuberances with each of the one or more recesses in a snap-fit connection.

20. The method of claim 15, wherein the collet includes the one or more protuberances, the one or more protuberances comprising a ledge disposed along a bottom edge of the lower section.

* * * * *